US011768152B2

(12) United States Patent
Takahashi et al.

(10) Patent No.: US 11,768,152 B2
(45) Date of Patent: Sep. 26, 2023

(54) INFORMATION PROCESSING SYSTEM AND SPECTROSCOPIC MEASURING INSTRUMENT

(71) Applicant: National University Corporation Hokkaido University, Hokkaido (JP)

(72) Inventors: Yukihiro Takahashi, Sapporo (JP); Tatsuharu Ono, Sapporo (JP); Nobuyasu Naruse, Otsu (JP); Yurino Ishida, Sapporo (JP)

(73) Assignee: NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 0 days.

(21) Appl. No.: 17/686,021

(22) Filed: Mar. 3, 2022

(65) Prior Publication Data

US 2023/0251185 A1    Aug. 10, 2023

(30) Foreign Application Priority Data

Feb. 7, 2022    (JP) ................................. 2022-017173

(51) Int. Cl.
*G01N 21/31*    (2006.01)
*G01N 33/00*    (2006.01)
*G01N 21/03*    (2006.01)

(52) U.S. Cl.
CPC .......... *G01N 21/03* (2013.01); *G01N 33/0098* (2013.01); *G06T 2207/30188* (2013.01)

(58) Field of Classification Search
CPC .......................... G01N 21/31; G01N 33/0098
See application file for complete search history.

(56) References Cited

U.S. PATENT DOCUMENTS

2013/0217439 A1*  8/2013  Ulman ................ H04N 23/11
                                                        455/556.1
2019/0219499 A1*  7/2019  Gold .................... G06T 7/0002
(Continued)

FOREIGN PATENT DOCUMENTS

CN    113159420          7/2021
CN    113159420 A    *   7/2021
(Continued)

OTHER PUBLICATIONS

Stroppiana, D. et al. "Plant nitrogen concentration in paddy rice from field canopy hyperspectral radiometry." Field crops research 111.1-2 (2009): 119-129 (Year: 2009).*

(Continued)

*Primary Examiner* — Tarifur R Chowdhury
*Assistant Examiner* — Roberto Fabian, Jr.
(74) *Attorney, Agent, or Firm* — Wenderoth, Lind & Ponack, L.L.P.

(57) ABSTRACT

An information processing system includes a storage, an interface device, and a computing circuit. The storage stores a database, in which spectrum data concerning light from a light source and a measurement condition data at a time of measurement of the light are associated with a plant status data concerning growth of a plant and/or a harvest data concerning a harvest of the plant. The interface device receives an input of a user measurement condition which is to be applied at a time of measurement of the plant by a user and which includes data concerning angles at the time of measurement and data concerning a plant status and/or a harvest to be predicted. The computing circuit determines at least two wavelengths contained in the light from the light source to be measured under the user measurement condition by referring to the database based on the user measurement condition.

20 Claims, 21 Drawing Sheets

(56) References Cited

U.S. PATENT DOCUMENTS

| | | |
|---|---|---|
| 2020/0242808 A1 | 7/2020 | Watanabe et al. |
| 2020/0319024 A1 | 10/2020 | Takahashi et al. |
| 2021/0027056 A1 | 1/2021 | Koch et al. |
| 2021/0365683 A1 | 11/2021 | Badhwar et al. |
| 2022/0092871 A1 | 3/2022 | Toizumi et al. |

FOREIGN PATENT DOCUMENTS

| | | | |
|---|---|---|---|
| JP | 2010-166851 | | 8/2010 |
| JP | 2010166851 A | * | 8/2010 |
| JP | 6342594 | | 5/2018 |
| JP | 2020-122681 | | 8/2020 |
| JP | 2021-171057 | | 11/2021 |
| JP | 2021-174062 | | 11/2021 |
| WO | 2016/181743 | | 11/2016 |
| WO | 2020/161812 | | 8/2020 |

OTHER PUBLICATIONS

Pullanagari, R. R., et al. "Multi-spectral radiometry to estimate pasture quality components." Precision Agriculture 13.4 (2012): 442-456 (Year: 2012).*

Extended European Search Report dated Aug. 22, 2022 in European Patent Application No. 22159557.2.

Stroppiana, Daniela et al., "Plant nitrogen concentration in paddy rice from field canopy hyperspectral radiometry", Field Crops Research, Mar. 15, 2009, vol. 111, No. 1-2, , pp. 119-129.

Pullanagari, R. R. et al., "Multi-spectral radiometry to estimate pasture quality components", Precision Agriculture, Kluwer Academic Publishers, Mar. 2, 2012, vol. 13, No. 4, pp. 442-456.

Notice of Grounds for Rejection dated Aug. 30, 2022 in Japanese Patent Application No. 2022-017173, with English-language concise explanation.

* cited by examiner

FIG. 2

| ENTRY | DATE & TIME | LAT. & LONG. | ALT. | SPECTRAL DATA | | | MEASUREMENT CONDITION DATA | | | PLANT STATUS DATA | | | | HARVEST DATA | |
|---|---|---|---|---|---|---|---|---|---|---|---|---|---|---|---|
| | | | | λ | REFLECTION INTENSITY OF PLANT $O(\lambda)$ | INTENSITY OF SUNLIGHT $S(\lambda)$ | PHOTO DATA | AZIMUTHAL ANGLE DIFFERENCE (Az) BETWEEN SUN AND INSTRUMENT | EL. ANGLE OF INSTRUMENT ($\theta$1) | EL. ANGLE OF SUN ($\theta$2) | SPREAD OF LIGHT SOURCE | GROWTH STATUS | PEST | CONTAINED COMPONENTS | SOIL CONDITION | AMT. OF HARVEST | HARVEST TIME |
| 1 | | | | λ1 | $O(\lambda1)$ | $S(\lambda1)$ | FARM FIELD IMAGE | | | | | | | | | | |
| | | | | λ2 | $O(\lambda2)$ | $S(\lambda2)$ | | | | | | | | | | | |
| | | | | · | · | · | SHADOW IMAGE | | | | | | | | | | |
| | | | | λ100 | $O(\lambda100)$ | $S(\lambda100)$ | | | | | | | | | | | |
| 2 | | | | | | | | | | | | | | | | | |
| : | | | | | | | | | | | | | | | | | |
| 10 | | | | | | | | | | | | | | | | | |
| 11 | | | | | | | | | | | | | | | | | |
| : | | | | | | | | | | | | | | | | | |
| n | | | | | | | | | | | | | | | | | |

DB1

θ3=5°

θ3=15°

θ3=28°

θ3=37°

θ3=48°

AMOUNT OF HARVEST
[kg/10a]

(a)　　　　　(b)　　　　　(c)

(a)　　　　　(b)　　　　　(c)

INFORMATION PROCESSING SYSTEM AND SPECTROSCOPIC MEASURING INSTRUMENT

CROSS-REFERENCE TO RELATED APPLICATION

The present application is based upon and claims priority of Japanese Patent Application No. 2022-017173 filed on Feb. 7, 2022, the entire content of which is incorporated herein by reference.

BACKGROUND

1. Technical Field

The present disclosure relates to an information processing system and a spectroscopic measuring instrument.

2. Related Art

Japanese laid-open patent publication No. 2020-122681 (herein referred to as "Patent Document 1") discloses a technology for obtaining information on a type and characteristics of a measuring target by radiating light to image the measuring target. More specifically, the information system of Patent Document 1 has a database that contains spectral information of an article including the measuring target to be identified. The database also contains information on a specific wavelength range or a specific wavelength at which the measuring target can be identified. The information system receives reflected light from the measuring target and acquires spectral information (i.e., spectral image) by imaging the light within a specific wavelength range. The information system identifies the imaged measuring target using the acquired spectral image and the database, and obtains information on a type and characteristics of the measuring target and its presence or absence in the imaged area.

In Patent Document 1, a specific wavelength capable of identifying the measuring target is obtained in advance, and the measuring target is identified by use of light detected as having a specific wavelength. The specific wavelength is predetermined for each measuring target and is fixed regardless of the measurement conditions. Further, although the technology of Patent Document 1 can obtain the characteristics of the current measuring target and the like, it cannot determine what kind of characteristics the measuring target will have in the future.

SUMMARY

One of the objects of the present disclosure is to determine wavelengths required to obtain information about the future status and/or harvests of the plant, taking the measurement conditions into account. Another object of the present disclosure is to predict a plant status and/or harvest in the future from the wavelengths thus determined.

An information processing system according to one aspect of the present disclosure includes: a storage, an interface device, and a computing circuit. The storage stores a database, in which spectrum data concerning light from a light source and a measurement condition data at a time of measurement of the light are associated with a plant status data concerning growth of a plant and/or a harvest data concerning a harvest of the plant. The interface device receives an input of a user measurement condition which is to be applied at a time of measurement of the plant by a user and which includes data concerning angles at the time of measurement and data concerning a plant status and/or a harvest to be predicted. The computing circuit determines at least two wavelengths contained in the light from the light source to be measured under the user measurement condition by referring to the database based on the user measurement condition.

In the information processing system according to one aspect of the present disclosure, the computing circuit: selects pairs of two wavelengths, the two wavelengths being different from one another and selected among the plurality of wavelengths; calculates an index value for each of the pairs at each of a plurality of sites; obtains a plant status and/or harvest at each of the plurality of sites; calculates a correlation coefficient indicating a degree of correlation between the index value and the plant status and/or harvest; and determines, as the at least two wavelengths, a pair of the two wavelengths whose correlation coefficient is equal to or more than 0.7.

A spectroscopic measuring instrument according to one aspect of the present disclosure includes an optical filter that allows the light with the at least two wavelengths determined by the above information processing system to pass through, and an image sensor that detects the light with the at least two wavelengths.

An information processing system according to one aspect of the present disclosure includes: a storage that stores a database, in which spectrum data concerning light from a light source and a measurement condition data at a time of measurement of the light are associated with a plant status data concerning growth of a plant and/or a harvest data concerning a harvest of the plant; an interface device that receives an input of a measurement condition at a time of measurement of the plant using the above spectroscopic measuring instrument, the measurement condition including data of:

an intensity of light with the at least two wavelengths at the measurement;

an intensity of reflected light from the plant;

an azimuthal difference between the light source and the spectroscopic measuring instrument;

an elevation angle of the spectroscopic measuring instrument; and an elevation angle of the light source, a computing circuit that predicts a plant status and/or a harvest in the future by referring to the database based on the measurement condition and each value of the at least two wavelengths.

According to a certain aspect of the present disclosure, it is possible to determine wavelengths required to obtain information about future status and/or a harvest of a plant, taking measurement conditions into account. Further, according to another aspect of the present disclosure, it is possible to predict a future status and/or harvest of the plant from the wavelengths thus determined.

BRIEF DESCRIPTION OF DRAWINGS

FIG. 2 is a diagram showing an exemplary data structure of a database according to an exemplary embodiment.

DETAILED DESCRIPTION

The embodiments will be described in detail with reference to the drawings as appropriate. However, more detailed explanations than are necessary may be omitted. For example, in some cases, detailed explanations of already well-known matters and duplicate explanations for substantially identical configurations are omitted. This is to avoid unnecessary redundancy in the description below and to facilitate the understanding of those skilled in the art.

The inventor(s) have provided the accompanying drawings and the following description in order for those skilled in the art to fully understand the present disclosure. They should not be interpreted as limiting the subject matter described in the claims. In each of the following embodiments, a translation apparatus will be described as an embodiment(s) of a speech processing apparatus.

1. EMBODIMENT

[1.1 Configuration]
[1.1.1 Overall Configuration]

Figure 1:
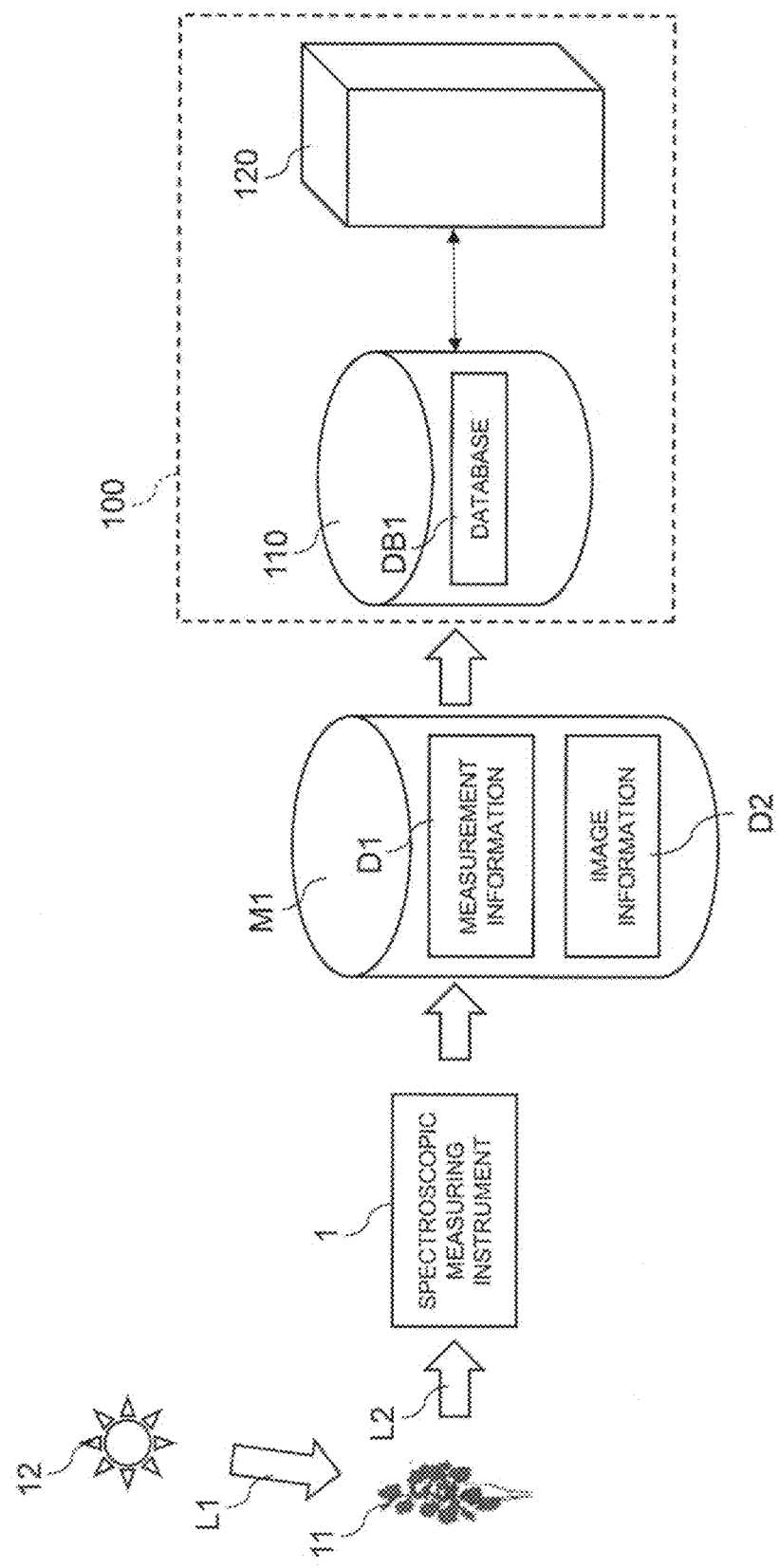
FIG. 1 is a schematic diagram illustrating a usage example of a spectroscopic measuring instrument according to an exemplary embodiment.

FIG. 1 is a schematic diagram illustrating a usage example of a spectroscopic measuring instrument 1 according to a present embodiment. The spectroscopic measuring instrument 1 measures reflection spectrum of object 11 with respect to light source 12.

In the present embodiment, the object 11 is rice. The object 11 may be a crop other than rice. The object 11 may be a plant other than a crop. The object 11 may be a colony rather than an individual. For example, the object 11 may be not a single tree but a plurality of trees or forests existing within the measurement range. Further, the object 11 may be grass.

In this embodiment, the light source 12 is the sun. The light source 12 is not limited to the sun, and can be selected from various light sources such as halogen lamps, LED lamps, ultraviolet lamps, and infrared lamps. The light source 12 may be selected so that a reflection spectrum in a desired wavelength range can be obtained from the object 11.

Results of the measurement by the spectroscopic measuring instrument 1 is used for processing in the information processing system 100. The spectroscopic measuring instrument 1 provides information to be processed by the information processing system 100.

The information processing system 100 executes various information processing related to the object 11. The information processing system 100 of FIG. 1 includes a database device 110 and a server device 120.

The database device 110 can be built by one or more computer systems. The database device 110 stores database DB1. The database DB1 can be used for information processing that can be executed by the server device 120. The database DB1 is a set of information used by the server device 120. The database DB1 may be herein referred to as a library DB1.

FIG. 2 shows an exemplary data structure of the database DB1 according to the present embodiment. The database DB1 contains a plurality of records (i.e., entries) related to the plant which is the object 11. Each of the plurality of records includes spectral data, measurement condition data, plant status data, and harvest data.

The spectrum data includes the reflection spectrum data of the object 11 and the spectrum data of the light source 12. The data of the reflection spectrum of the object 11 indicates an intensity (reflection intensity: O(.)) of the light from the light source 12 reflected by the object 11 at a predetermined wavelength interval in a predetermined wavelength range. The spectral data of the light source 12 indicates an intensity (S(.)) Of the light from the light source 12 at a predetermined wavelength interval in a predetermined wavelength range. The predetermined wavelength range is, for example, about 420 nm to about 840 nm, and the predetermined wavelength interval is, for example, about 4 nm. In FIG. 2, wavelengths $\lambda 1$ to $\lambda 100$ fall within a predetermined wavelength range and represent wavelengths at predetermined wavelength intervals. For the wavelength $\lambda$ ($\lambda=\lambda 1, \lambda 2, \ldots, \lambda 100$), the reflection intensity ($O(\lambda)$) of the target plant and the intensity $S(\lambda)$ of the sunlight as a light source are acquired and described. In this embodiment, the spectral data may include data relating to an image. Examples of the image include an image related to the object 11 and an image related to the light source 12. In FIG. 2, a plurality of wavelengths are described in one entry, and the reflection intensities $O(\lambda)$ and intensities $S(\lambda)$ are described for each wavelength. This indicates that the wavelengths are acquired in one measurement using the spectroscopic measuring instrument 1, which forms a wavelength band extending from wavelengths $\lambda 1$ to $\lambda 100$.

The measurement condition data indicates conditions related to the measurement for obtaining the spectral data. The reflection spectrum of the object 11 with respect to the light source 12 measured by the spectroscopic measuring instrument 1 may be affected by a positional relationship between the light source 12 and the spectroscopic measuring instrument 1. That is, if the positional relationship between the light source 12 and the spectroscopic measuring instrument 1 differs, the reflection spectrum measured by the spectroscopic measuring instrument 1 may differ even for the same object 11. In order to correctly evaluate the reflection spectrum of the object 11 with respect to the light source 12, it is preferable to use information on the positional relationship between the light source 12 and the spectroscopic measuring instrument 1 at the time of measurement of the reflection spectrum.

Figure 3:
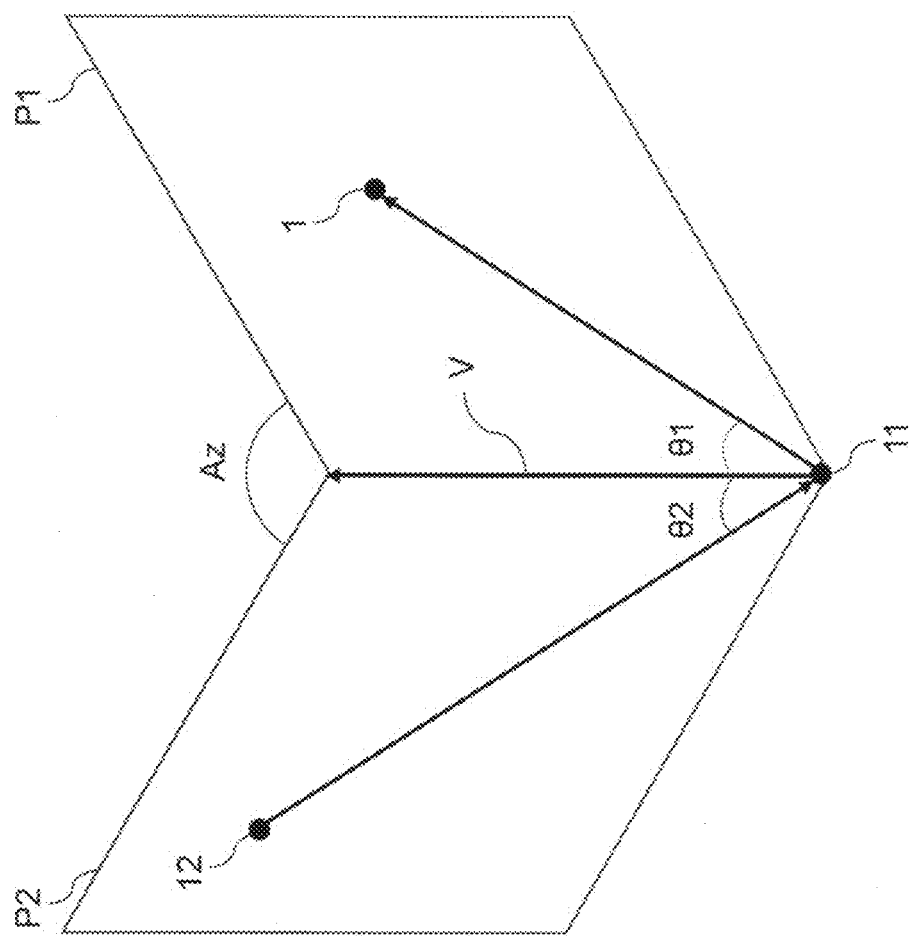
FIG. 3 is a diagram illustrating measurement of a reflection spectrum of light from an object reflecting light radiated from a light source by use of the spectroscopic measuring instrument.

FIG. 3 is an explanatory diagram of measurement of the reflection spectrum from the object 11 with respect to the light source 12 by the spectroscopic measuring instrument 1. The positional relationship between the light source 12 and the spectroscopic measuring instrument 1 is specified by an angle of the spectroscopic measuring instrument 1 with respect to the object 11, an angle of the light source 12 with respect to the object 11, and an azimuthal angle difference between the light source 12 and the spectroscopic measuring instrument 1. The angle of the spectroscopic measuring instrument 1 with respect to the object 11 can be represented by, for example, the angle $\theta 1[°]$ of the spectroscopic measuring instrument 1 with respect to the vertical direction V or the angle of the spectroscopic measuring instrument 1 with respect to the horizontal plane ($90°-\theta 1$). The angle of the light source 12 with respect to the object 11 can be expressed, for example, by the angle $\theta 2$ [°] of the light source 12 with respect to the vertical direction V or the angle of the light source 12 with respect to the horizontal plane ($90°-\theta 2$). The azimuthal angle difference between the light source 12 and the spectroscopic measuring instrument 1 is, for example, a vertical plane P1 including the spectroscopic measuring instrument 1 and the object 11 and orthogonal to the horizontal plane, and a vertical plane P1 including the light source 12 and the object 11 and orthogonal to the horizontal plane. It can be represented by an angle Az [°] with respect to the vertical plane P2. In FIG. 3, Az is defined as increasing counterclockwise.

In the present embodiment, the measurement condition data includes, for example, the azimuthal angle difference (Az) between the light source 12 and the spectroscopic measuring instrument 1, the angle ($\theta 1$) of the spectroscopic measuring instrument 1 with respect to the object 11, and an angle ($\theta 2$) of the light source 12 with respect to the object 11.

Further, the measurement condition data relates to the condition or status of the light source 12 at the time of measurement. For example, the measurement condition data includes an evaluation value of the spread of the light source 12. The evaluation value of the spread of the light source 12 indicates the degree of light scattering from the light source 12 due to the surrounding environment of the object 11. The degree of light scattering from the light source 12 due to the surrounding environment of the object 11 is affected by the transparency of the atmosphere, weather (for example, the number of clouds), amount of aerosol in the atmosphere, and the like. As an example, the evaluation value of the spread of the light source 12 is can be expressed as a ratio of scattered light component with respect to direct light component. The scattered light component can be obtained as an amount of light scattered by the surrounding environment of the object 11. The direct light component can be obtained as an amount of light that directly reaches the object 11 from the light source 12. How the light hits the object 11 from the light source 12 is influenced by the surrounding environment of the object 11. For example, the way the light from the light source 12 hits the object 11 changes between sunny weather and cloudy weather. In fine weather, it can be considered that the light source 12 hits the object 11 in one direction, but in cloudy weather, the light from the light source 12 is scattered by the clouds, and the light source 12 to the object 11 is in all directions in some cases. Comparing the sunny weather and the cloudy weather, the reflection spectrum is more likely to be affected by the positional relationship between the light source 12 and the spectroscopic measuring instrument 1 in the sunny weather than in the cloudy weather. Therefore, in order to correctly evaluate the reflection spectrum of the object 11 with respect to the light source 12, it is preferable that the measurement condition data includes the evaluation value of the spread of the light source 12. The evaluation value of the spread of the light source 12 makes it possible to quantify or discriminate the degree of cloudiness in fine weather and cloudy weather. The method of acquiring the reflection spectrum may be changed according to the degree of cloudiness in fine weather and cloudy weather. For example, the recommended angle for acquiring the reflected light may be narrower than the standard in fine weather and wider than the standard in cloudy weather.

As shown in FIG. 2, it is preferable that the database DB1 contains a plurality of records, which contains, for the same object 11 (plant), different types of combinations of, at least: the azimuthal angle difference (Az) between the light source 12 (sun) and the spectroscopic measuring instrument 1; the angle of the spectroscopic measuring instrument 1 with respect to the object 11; and the angle of the light source 12 (sun) with respect to the object 11 (elevation angle: $\theta 2$). For example, it is preferable that the plurality of records exist so that Az, $\theta 1$ and $\theta 2$ are different every 20°, preferably every 10°, and more preferably every 5°, respectively.

The status data shows the status related to the object 11. In the present embodiment, the object 11 is rice, and the status data relates to a status concerning to rice that can change with time. Examples of the status data include an evaluation value regarding the growth status, an evaluation value regarding the disease and pest, an evaluation value regarding the contained components, and an evaluation value regarding the soil condition. The status data can be obtained by performing an inspection or the like at the time of measurement for obtaining spectral data.

The result data shows the result regarding the object 11. The results for the object 11 relate, for example, to the end point of the status of the object 11. In the present embodiment, the object 11 is rice, and the result data may include data on harvesting, which is the end point of the growing status of rice. Examples of result data include amount of harvest and harvest time. Hereinafter, the phrase "amount of harvest" will also referred to as "harvest amount". The resulting data can be generated when the rice is actually harvested, not at the time of measurement to obtain spectral data. The harvest is measured by actually harvesting the rice, and the harvest time can be determined based on the date when the rice was actually harvested.

The server device 120 (FIG. 1) can be constructed by one or more computer systems. The server device 120 may be communicably connected to the database device 110 via a wired or wireless network. The server device 120 includes a storage interface to which the computer-readable medium 40 described later is detachably connected.

The server device 120 manages the database DB1, determines two or more wavelengths using the database DB1 and user measurement conditions, infers using the acquired data of the two or more wavelengths and the database DB1, and constructs a learned model using the database DB1.

Management of database DB1 may include addition, deletion, and editing of records (entries) of database DB1. In the present embodiment, the server device 120 can add records by using the information obtained from the spectroscopic measuring instrument 1.

Determining two or more wavelengths using the database DB1 and user measurement conditions is to select two or more wavelengths to be measured when optically measuring a plant cultivated and cultivated by the user. The selected two or more wavelengths are used to determine one or more optical filters that transmit the light with the wavelengths. By measuring the plant using a spectroscopic measuring instrument or an image pickup device equipped with the optical filter(s), spectral data of a desired wavelength can be obtained from the light reflected by the plant, and the inference described below will be done. The details of this process will be described later.

Inference using the database DB1 is a process of obtaining, a part or all of, status data or result data based on, a part or all of, given spectral data and measurement condition data. From the database DB1, status data or result data is associated with the combination of the spectrum data and the measurement condition data. Therefore, it is possible to predict the status data and/or the result data corresponding to the set from the set of the spectrum data and the measurement condition data that do not exist in the database DB1.

The generation of a learned model using the database DB1 may include generation of a learned model that executes inference using the database DB1. The server device 120 generates a training data set from the database DB1, for example, using spectrum data and measurement condition data as explanatory variables, status data, or result data as objective variables. The server device 120 can generate a learned model by using a data set for learning to generate learned parameters and incorporating the learned parameters into an inference program.

[1.1.2 Database Based on the Knowledge of the Present Inventors]

The present inventors have conducted various studies and found that the growing status of the plant as the object 11 can be detected by irradiating the plant with the light from the light source 11 and observing the reflected light. However, in that case, it was concluded that it is necessary to classify the cases according to various conditions. The conditions include the variety of the plant, the angle at which the light source 12 shines light on the plant which is the object 11, the angle at which the reflected light from the plant is measured by the spectroscopic measuring instrument 1, the timing of measurement, and the like. Hereinafter, a specific description will be given.

Figure 4:
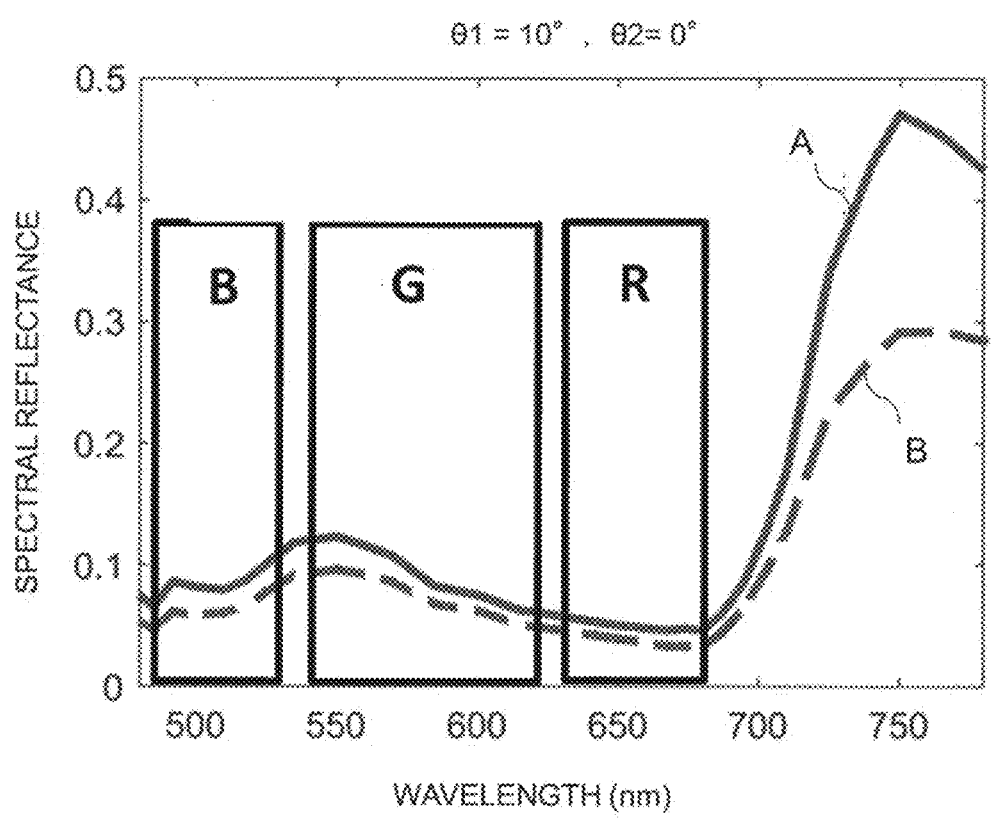
FIG. 4 is a graph showing wavelength-spectral reflectance characteristics of radish sprout in healthy and water shortage conditions.

FIG. 4 is a graph showing the wavelength-spectral reflectance characteristics of radish sprouts in health and water shortage conditions. The horizontal axis of the graph represents wavelength, and the vertical axis represents spectral reflectance. The spectral reflectance is determined for each of the wavelength bands of 460 nm to 780 nm. The solid line A shows the spectral reflectance characteristics of healthy radish sprouts, and the broken line B shows the spectral reflectance characteristics of radish sprouts due to water shortage. "B", "G" and "R" indicate approximate wavelength ranges of blue, green and red, respectively. A liquid crystal tunable filter (LCTF) camera was adopted as the spectroscopic measuring instrument 1. A halogen lamp was adopted as the light source 12.

The spectrum of radish sprouts in health and water shortage conditions is significantly higher in infrared range, which has longer wavelengths than those in the red wavelength range.

It is understood that there is a marked difference in the infrared region. Therefore, it is understood that whether or not radish sprouts are currently healthy can be determined by using the spectral reflectance at wavelengths in the infrared region.

The spectral reflectance is determined by (intensity of reflected light/intensity of light from a light source). The intensity of the reflected light and the intensity of the light from the light source vary depending on the angle at which the light from the light source is applied to the radish sprouts and the position where the reflected light is measured.

Figure 5:
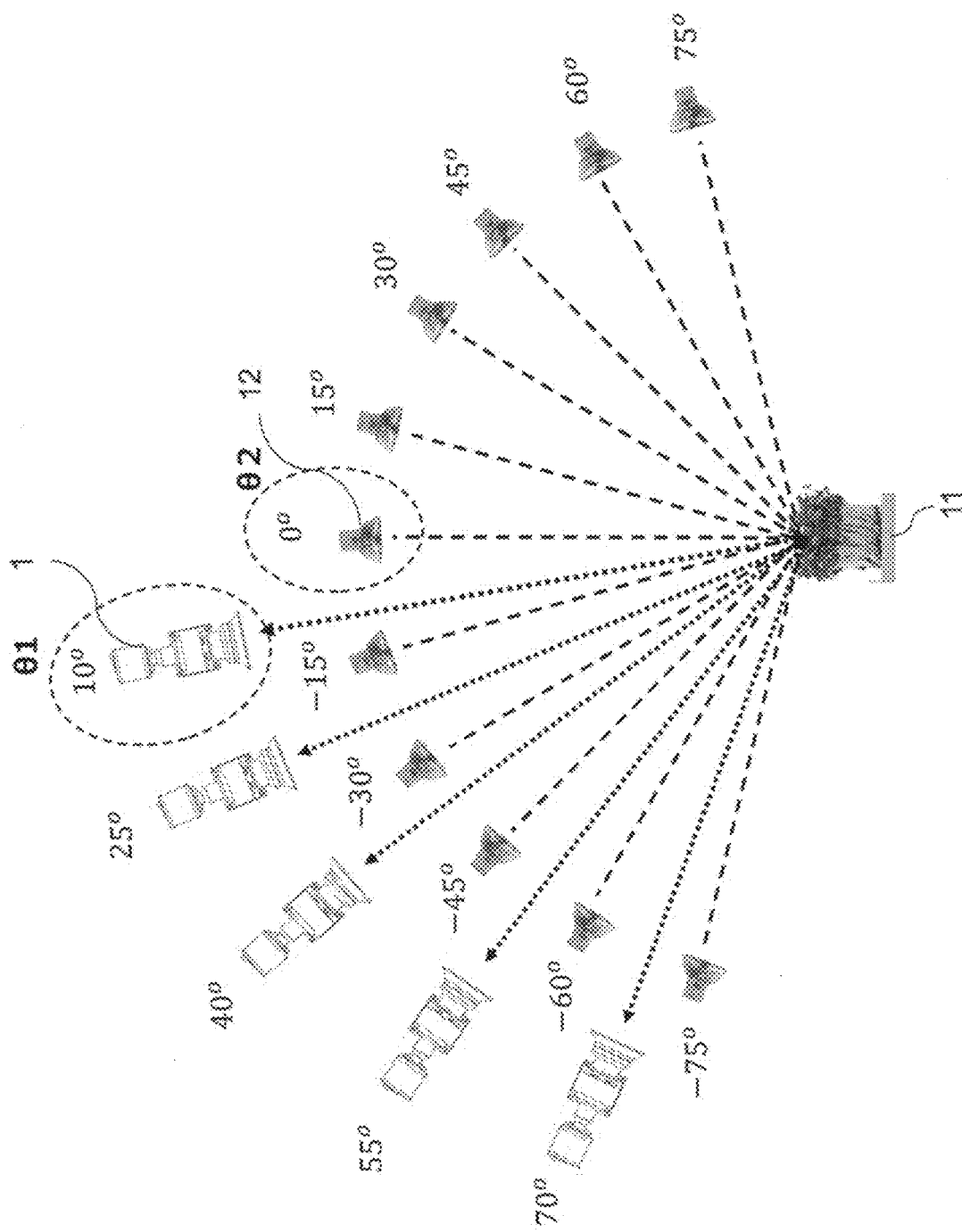
FIG. 5 is a diagram showing an example of a possible angle (θ2) of a light source with respect to a radish sprout as an object and a possible angle (θ1) of an LCTF camera as a spectroscopic measuring instrument for measuring reflected light.

FIG. 5 shows an example of a possible angle (θ2) of the halogen light source 12 with respect to the radish sprouts which is the object 11 and a possible angle (θ1) of the LCTF camera which is the spectroscopic measuring instrument 1 for measuring the reflected light. Of these, the graph of FIG. 4 is an example of measurement under the measurement conditions of θ1=10° and θ2=0°. It should be noted that these angles mean the angles θ1 and θ2 shown in FIG. 3.

The present inventors verified that the spectral reflectance has azimuthal dependency by fixing the angle θ2 of the light source 12 and by changing the angle 91 of the spectroscopic measuring instrument 1.

Figure 6A:
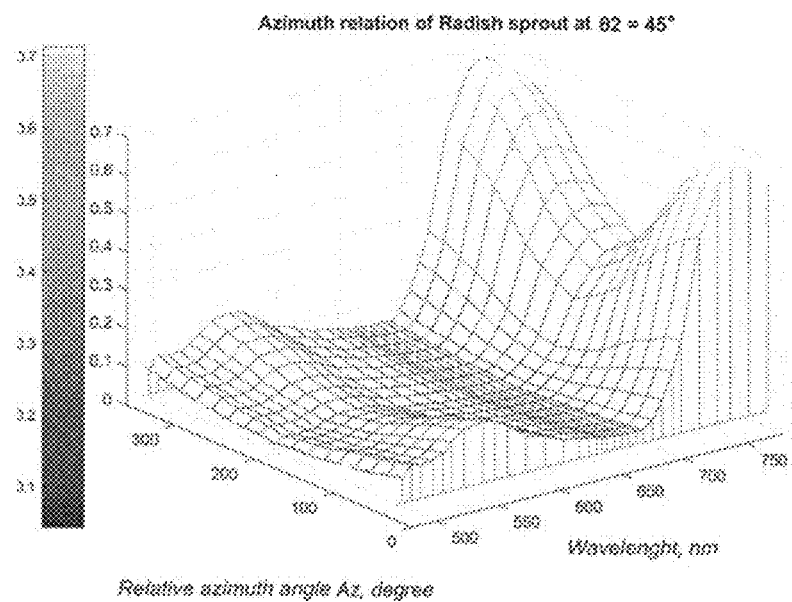
FIG. 6A is a three-dimensional graph showing differences in spectral reflectance for radish sprout depending on the angle.
Figure 6B:
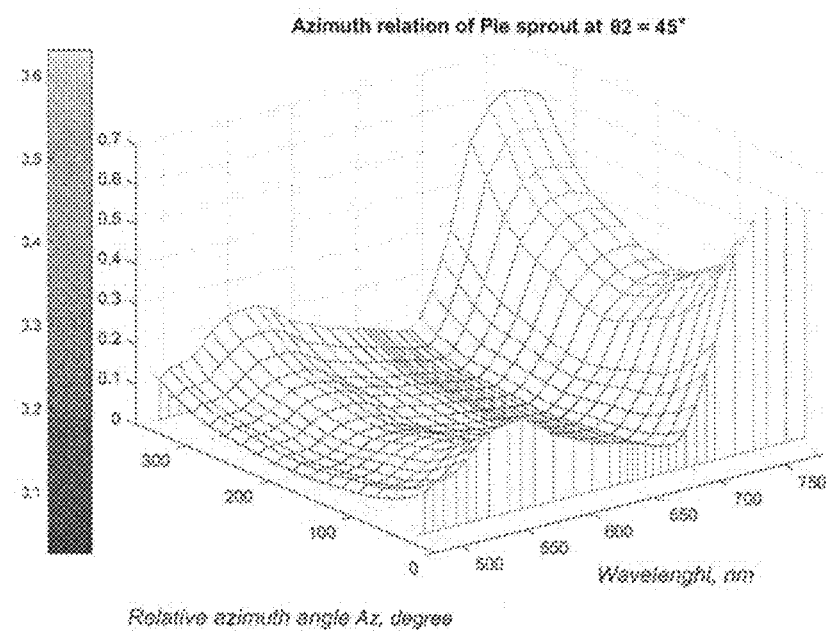
FIG. 6B is a three-dimensional graph showing the differences in spectral reflectance for bean seedlings depending on the angle.

FIG. 6A is a three-dimensional graph showing differences in spectral reflectance depending on the angle of radish sprouts. Further, FIG. 6B is a three-dimensional graph showing differences in spectral reflectance depending on the angle of the bean sprouts. The three-dimensional graph is stretched by an axis showing a wavelength from 460 nm to 780 nm, an axis showing an angle from 0° to 360°, and an axis showing a spectral reflectance from 0 to 0.7. The angle θ2 of the light source 12 is fixed at 45°. From the figure, when the angle θ1 of the spectroscopic measuring instrument 1 is changed from 45° to 45° via 360° (=0°), the relative azimuthal angle (Az) between the spectroscopic measuring instrument 1 and the light source 12 varies from 0° to 360°. As shown in FIGS. 6A and 6B, it is understood that the spectral reflectance changes when the relative azimuthal angle between the spectroscopic measuring instrument 1 and the light source 12 changes even at the same wavelength. The measurement environment is an indoor laboratory.

Further, by comparing FIGS. 6A and 6B, it is shown that the spectral status changes between the radish sprouts and the bean sprouts depending on the relative azimuthal angle between the spectroscopic measuring instrument 1 and the light source 12. That is, it can be said that the spectral reflectance measured differs depending on the type of plant even under the same measurement conditions.

Furthermore, the present inventors also verified the angle dependence of rice. In the schematic diagram shown in FIG. 3, the object 11 is one or a plurality of rice plants, and the light source 12 is the sun. At a certain time in the same field (rice field) where rice is cultivated, θ2 is a fixed value. That is, the angle between the rice, which is the object 11, and the spectroscopic measuring instrument 1 can change.

Figure 7:
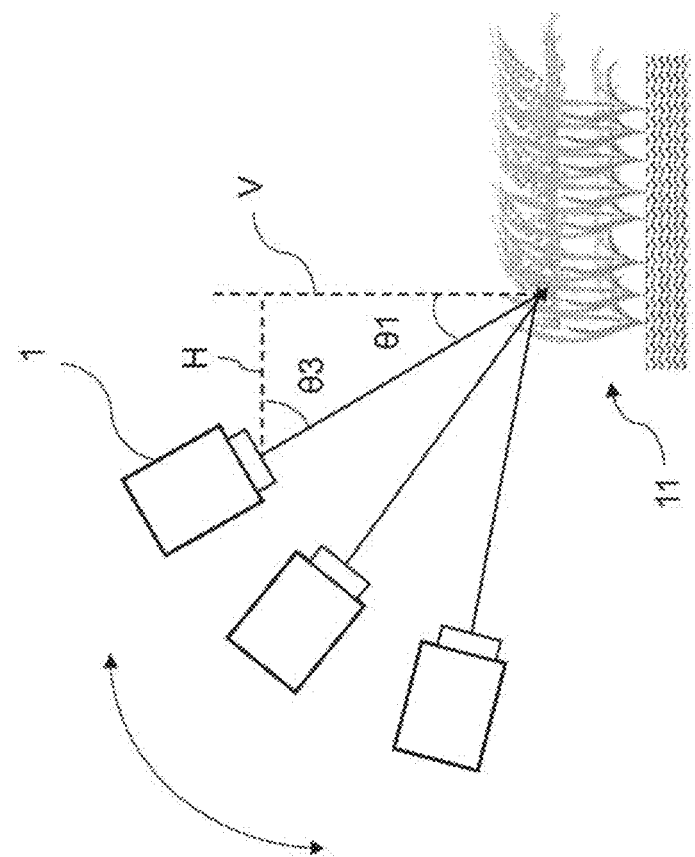
FIG. 7 is a diagram showing angles between the spectroscopic measuring instrument and a rice plant as an object.

FIG. 7 shows the angle between the spectroscopic measuring instrument 1 and the rice which is the object 11. In the example of FIG. 3, the angle of the spectroscopic measuring instrument 1 with respect to the object 11 is defined as the angle θ1 [°] of the spectroscopic measuring instrument 1 with respect to the vertical direction V. On the other hand, in FIG. 7, the angle of the spectroscopic measuring instrument 1 with respect to the object 11 can be defined by an angle θ3 (=90°−θ1), which is an angle of the spectroscopic measuring instrument 1 with respect to the horizontal plane H.θ3 can also be referred to as a "an angle of dip", or "a dip angle". For convenience of explanation, the following FIGS. 8A to 8E and FIG. 9 will be described with reference to the "dip angle", but the angle θ1 as the elevation angle may be used as described above.

Figure 8A:
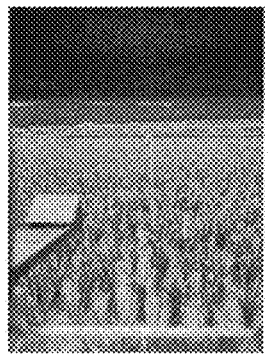
FIG. 8A shows an image of rice plant acquired by a spectroscopic measuring instrument when a dip angle is 5°.
Figure 8B:
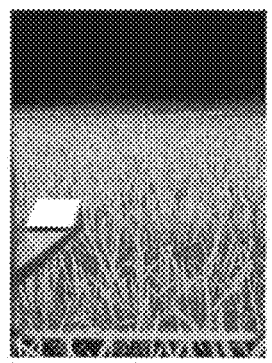
FIG. 8B shows an image of rice plant acquired by a spectroscopic measuring instrument when a dip angle is 15°.
Figure 8C:
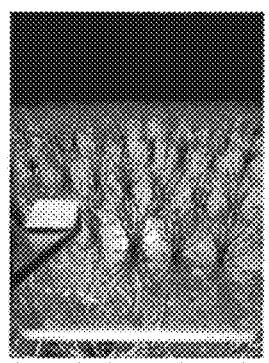
FIG. 8C shows an image of rice plant acquired by a spectroscopic measuring instrument when a dip angle is 28°.
Figure 8D:
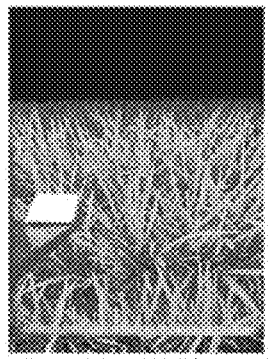
FIG. 8D shows an image of rice plant acquired by a spectroscopic measuring instrument when a dip angle is 37°.
Figure 8E:
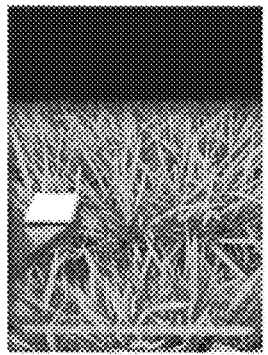
FIG. 8E shows an image of rice plant acquired by a spectroscopic measuring instrument when a dip angle is 48°.

FIGS. 8A to 8E show the difference in the rice images acquired by the spectroscopic measuring instrument 1 when the dip angles are different. FIG. 8A shows an image acquired at a dip angle of 5°. FIG. 8B shows an image acquired at a dip angle of 15°. FIG. 8C shows an image acquired at a dip angle of 28°. FIG. 8D shows an image acquired at a dip angle of 37°. The image is shown, and FIG. 8E shows the image acquired at a dip angle of 48°. The measurements in FIGS. 8A to 8E and 9 are the results of measurements in two fields, not in the same field.

Figure 9:
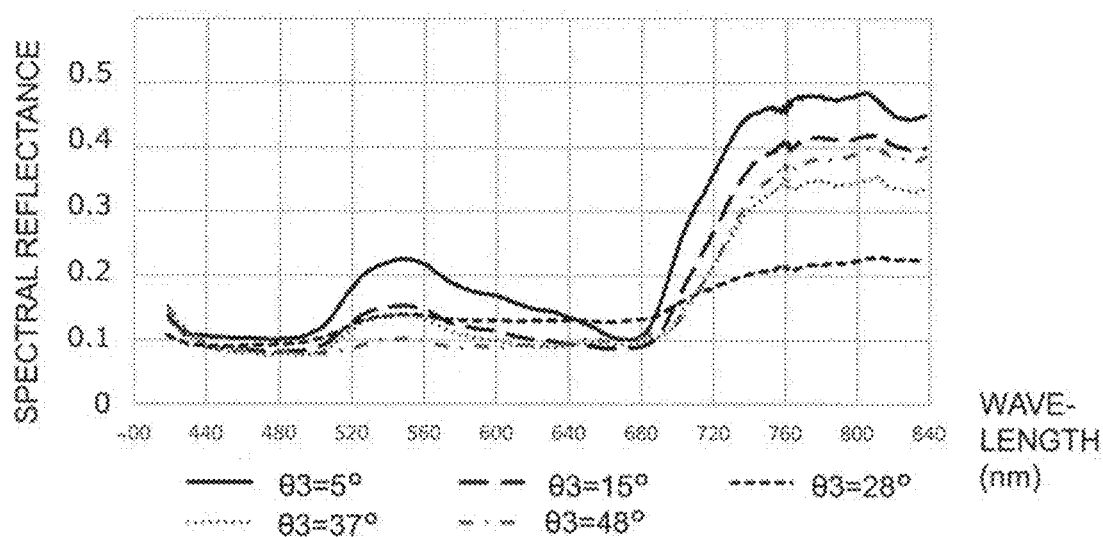
FIG. 9 is a graph showing changes in spectral reflectance depending on the dip angle.

FIG. 9 is a graph showing that the spectral reflectance changes according to the dip angle. When the dip angle is 28°, it is difficult to capture the change in spectral reflectance depending on the wavelength. On the other hand, at the dip angles of 5°, 15°, 37° and 48°, the spectral reflectance in the wavelength band of 680 nm or more and the spectral reflectance of less than 680 nm are significantly different.

By the way, when the dip angle becomes large, not only rice but also subjects other than the rice, such as water and soil, can come in the field of view of the spectroscopic measuring instrument 1. Therefore, it is appropriate that the dip angle is small so that only the original rice can be measured.

In consideration of these, the present inventors have determined that a dip angle of 15° or less is appropriate when acquiring the spectral reflectance of rice. In this way, it is possible to determine an appropriate dip angle not only in consideration of the spectral reflectance changing according to the wavelength but also in consideration of other measurement conditions.

Figure 10:
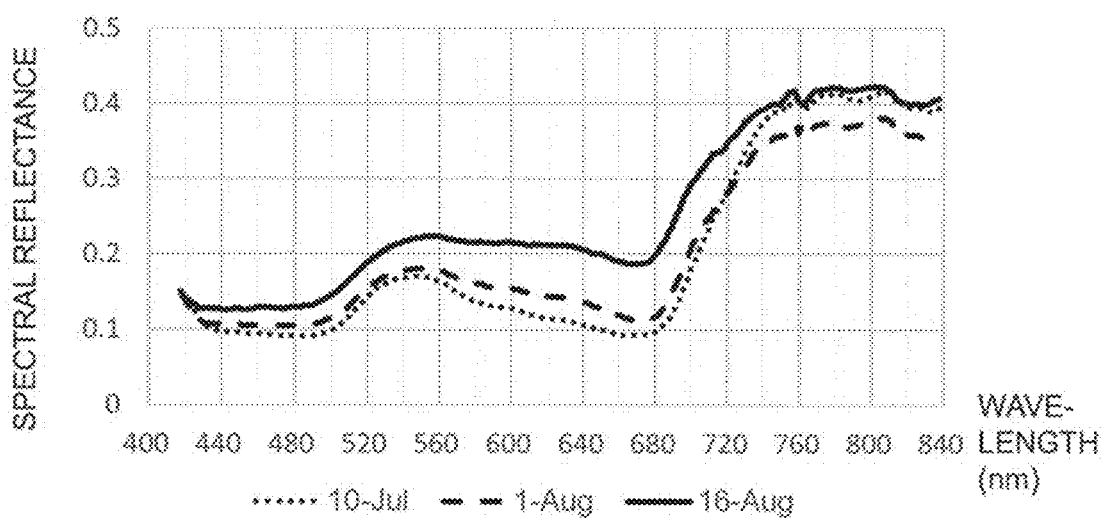
FIG. 10 is a graph showing that the spectral reflectance varies depending on the time of year of measurement.

FIG. 10 is a graph showing that the spectral reflectance differs depending on the measurement time. The thin broken line shows the spectral reflectance based on the measurement result of rice on July 10 of a certain year, the thick broken line shows the spectral reflectance on August 1 of the same year, and the solid line shows the spectral reflectance on August 16. It was confirmed that even for the same rice, the spectral reflectance differs depending on the time of measurement or the season.

Based on the above verification results, the present inventors decided to have the database DB1 shown in FIG. 2 contain spectral data, measurement condition data, plant status data, and harvest data for each entry. Also, the present inventors determined that each data may preferably include the following details.

Spectrum data: Multiple wavelengths contained in the light from the light source; the intensity of each wavelength; and the reflection intensity of the light of each wavelength reflected by the plant The light reflected in a plant contains both a component of the light due to specular reflection generated on the surface of the plant and a component of the light incident on the inside of the plant, scattered inside, and emitted from the surface again.

Measurement condition data: The elevation angle of the light source seen from the measuring instrument; the elevation angle of the measuring instrument; and the azimuthal angle difference between the measuring instrument and the light source at the time when the light is measured by the measuring instrument plant status data: At least one of the growth status of the plant; the status of pests that have occurred on the plant; the composition of the plant; and the status of the soil in which the plant has grown harvest data: Amount and time of harvest of the plant In addition to the entry number, data such as the date and time, longitude & latitude, and altitude of each entry may be included, or the entry number itself may include the date when the spectrum data of the entry was measured. In addition, both the vegetative status data and the harvest data may be included, or either one may be included. These may be determined in relation to the estimation process described later. That is, either one may be provided depending on whether the plant status is to be estimated from the current spectrum data and the measurement condition data of the plant, or the harvest is to be estimated.

In addition, in order to illustrate and explain rice in this embodiment, the database DB1 shown in FIG. 2 includes the illustrated vegetative status data and/or the harvest data. However, in the case of plants other than rice, other types of data may be included in the database DB1.

By constructing such a database DB1 in advance, the present inventors have realized the information processing system described below. Hereinafter, the configuration of the information processing system according to the present embodiment will be described.

[1.1.3 Information Processing System Configuration]

Figure 11:
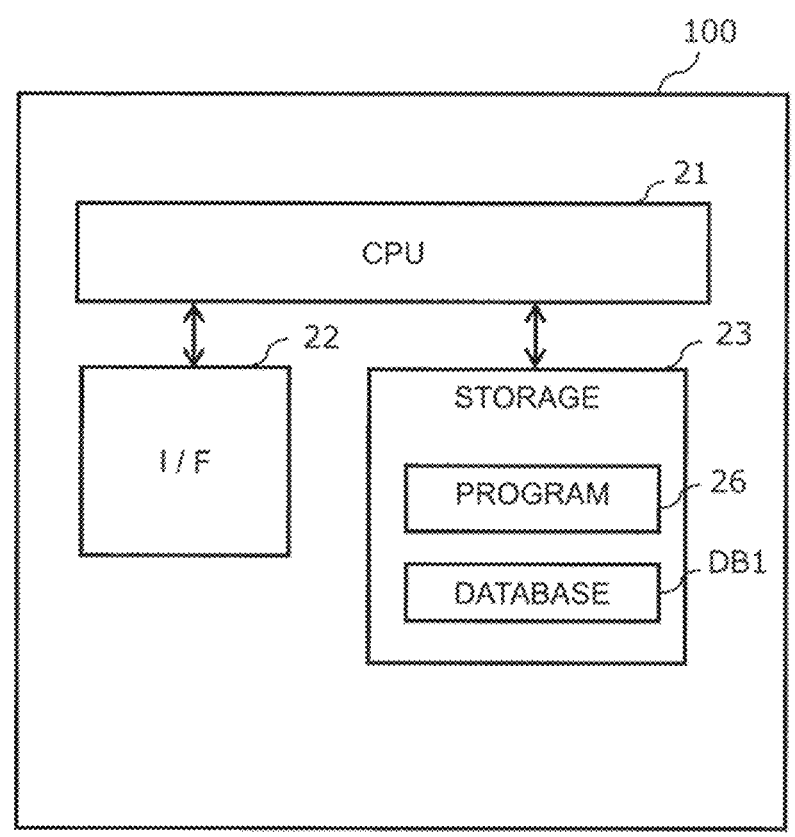
FIG. 11 is a block diagram illustrating a configuration of an information processing system according to an exemplary embodiment.

FIG. 11 shows the configuration of the information processing system 100 according to the present embodiment. The information processing system 100 is realized as, for example, one information processing device, and is typically a server computer.

The information processing system 100 includes a CPU 21 for performing calculations, an interface device (I/F) 22 for communicating with other devices, and a storage device 23 for storing a database DB1 and a computer program 26. Although it was explained that the database DB1 is stored in the database device 110 in FIG. 1, in the example of FIG. 11, the substance of the database device 110 is the storage device 23. Hereinafter, the computer program 26 is abbreviated as "program 26".

The CPU 21 is an example of the arithmetic circuit of the information processing system 100 in the present embodiment. The CPU 21 realizes the processing described later by executing the program 26 stored in the storage device 23. The arithmetic circuit configured as the CPU 21 in the present embodiment may be realized by various processors such as MPU or GPU, or may be configured by one or a plurality of processors.

The I/F 22 is a communication circuit that communicates in accordance with a standard such as a USB terminal, IEEE802.11, 4G, or 5G. The I/F 22 may be connectable to a communication network such as the Internet. Further, the information processing system 100 may directly communicate with other devices via the I/F 22, or may communicate via the access point. In this embodiment, the I/F 22 is used to receive input of data about the plant from a user who grows the plant.

The storage device 23 is a storage medium for storing data necessary for realizing the functions of the information processing system 100, and stores various data such as the program 26 executed by the CPU 21 and the database DB1. The storage device 23 is composed of, for example, a hard disk drive (HDD) or a solid status drive (SSD) which is a semiconductor storage device. The storage device 23 may include a temporary storage element configured by, for example, a RAM such as a DRAM or an SRAM, or may function as a work area of the CPU 21. The database DB1 is as described with reference to FIG. 2, and includes spectrum data, measurement condition data, plant status data, and harvest data.

Note that the database DB1 may include data on one specific type of plant or one type of plant, or may include data on each of various or many types of plants. For example, the database DB1 may be specialized for "Nanatsuboshi" which is one variety of rice, or may be specialized for "rice" of a plurality of varieties.

[1.2 Processing by Information Processing System]

Hereinafter, in the items [1.2.1] and [1.2.2], the processing using the information processing system 100 will be described. Item [1.2.1] describes the wavelength selection process using the information processing system 100. In the item [1.2.2], the estimation process regarding the future plant using the information processing system 100 will be described. In the following, each process of the items [1.2.1] and [1.2.2] will be described as a process of the same information processing system 100. However, the processing of both items does not necessarily have to use the common information processing system 100. In each process, a separate information processing system having the same configuration as the information processing system 100 can be used.

In the present embodiment, each of the procedures as described in items [1.2.1] and [1.2.2] is performed to predict the future status and/or harvest outcome (harvest amount and/or harvest time) from the data of the rice which is currently cultivated by the user who is a rice farmer. Needless to say, it is preferable to obtain highly accurate prediction results. Further, it is preferable that the data necessary for obtaining such a prediction result can be easily acquired so as to reduce the burden on the user. These can be realized by the processing of each item described below.

In the present embodiment, the user provides the "user measurement condition" to the operator of the information processing system 100. The "user measurement condition" is a condition applied at the time of measurement by the user. More specifically, the "user measurement condition" includes (1) data on the angle at the time of measurement and (2) data on the vegetative status and/or harvest to be predicted. The data in (1) corresponds to the "measurement condition data" in FIG. 2. Further, the data in (2) is data for specifying which of the "vegetative status data" and/or the "harvest data" in FIG. 2 is desired to be predicted.

The information processing system 100 has a plurality of wavelengths having a strong correlation with the future harvest amount and/or harvest time of rice when measured under the "user measurement conditions" by the processing of the item [1.2.1]. To be elected. When a plurality of wavelengths are selected, the operator or the like of the information processing system 100 sets one or a plurality of optical filters that transmit the plurality of wavelengths in the image pickup device, and mails the image pickup device to the user. Such an image pickup device is one aspect of a spectroscopic measuring instrument. The user may simply photograph the rice using the image pickup device under the measurement conditions that match the initially provided "user measurement conditions". The image pickup device detects light mainly containing the plurality of wavelengths by using the mounted image sensor, and stores the image information in the storage device or the memory card. That is, the image pickup device in which such an optical filter is set functions as a spectroscopic measuring instrument 1 that selects light having a transmission wavelength of the optical filter from incident light.

The user may provide the captured "image" to the operator of the information processing system 100. The method of the provision is not limited to a specific way. For example, the image may be provided by returning the image pickup device from the user to the operator of the information processing system 100 together with the acquired data stored in the device. Alternatively, it may be realized by the user extracting image information from the storage device of the image pickup device and transmitting it to the information processing system 100 via a communication line.

The information processing system 100 extracts image information mainly including the plurality of wavelengths, and predicts the future harvest amount and/or the harvest time of the rice by the processing of the item [1.2.2]. The information processing system 100 presents the prediction result to the user by a method such as a numerical value or a graph. The user can modify the current cultivation method or create a sales plan based on the prediction result.

Below, for convenience of explanation, an example of predicting the harvest amount of rice will be described.

[1.2.1 Wavelength Selection Processing Using Information Processing System]

Figure 12:
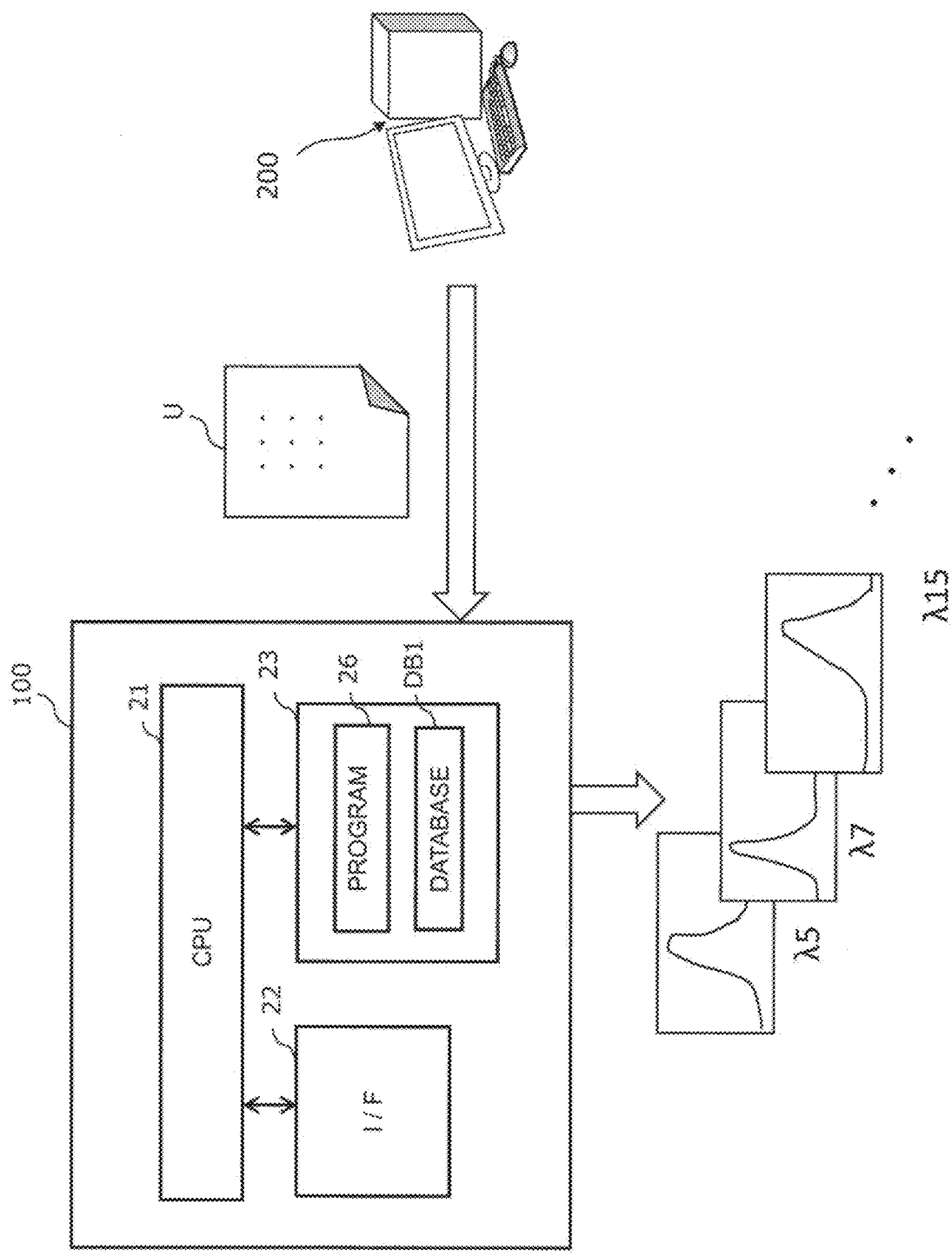
FIG. 12 is a hardware configuration diagram that can be used in a wavelength determination process in the information processing system.

FIG. 12 is a hardware configuration diagram used for wavelength selection processing using the information processing system 100. The information processing system 100 receives the data of the user measurement condition U from the user terminal 200. The user terminal 200 may be a PC, a smartphone, a tablet terminal, or the like.

Figure 13:
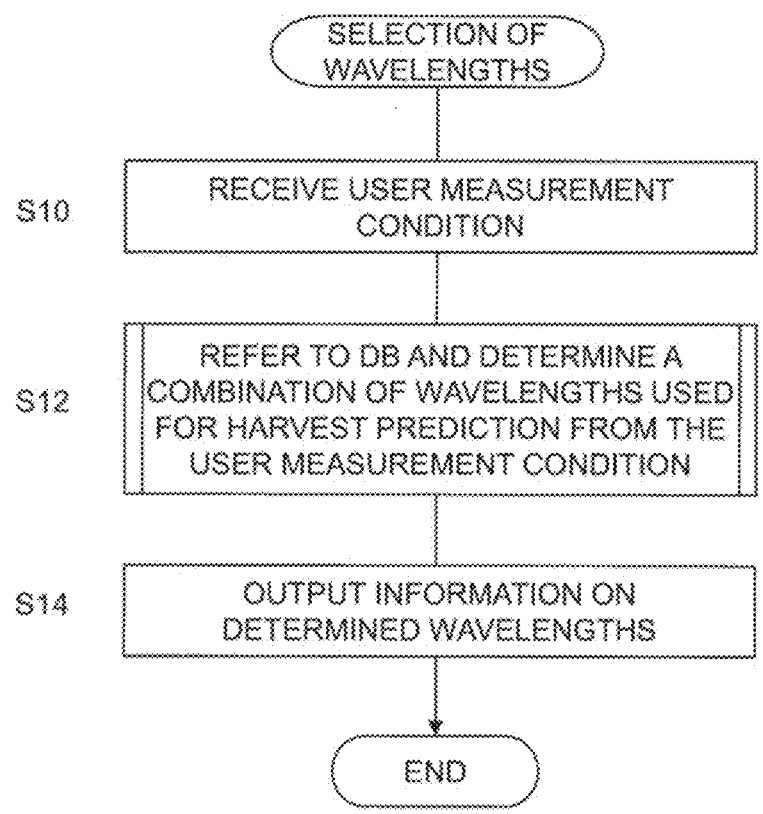
FIG. 13 is a flowchart showing a procedure of the information processing system for determining a plurality of wavelengths having a strong correlation with harvest amount of rice.

Further, FIG. 13 is a flowchart showing a processing procedure of the information processing system 100 for selecting a plurality of wavelengths having a strong correlation with the future harvest amount of rice.

In step S10, the CPU 21 of the information processing system 100 receives the input of the user measurement condition U from the user terminal 200 via the I/F 22. Examples of the user measurement condition U include the date and time when the user plans to measure rice, the azimuthal angle difference between the sun and the image pickup device (Az), the elevation angle of the image pickup device (θ1), and the elevation angle of the sun (θ2). Latitude and mildness of the field, arrangement, location, rice varieties, etc. The I/F 22 is, for example, a communication circuit.

In step S12, the CPU 21 refers to the database DB1 stored in the storage device 23, and refers to the wavelength λk (k=1, . . . , N; N is an integer that is equal to 2 or more) used for the harvest amount prediction from the user measurement condition U.

In step S14, the CPU 21 outputs information on the determined wavelengths via the I/F 22. The I/F 22 is, for example, a communication circuit or a monitor output terminal of an operator of the information processing system 100.

It is not necessary to output a specific value for each wavelength. For example, a wavelength band Bk having a predetermined width including a wavelength λk, for example, a spectrum half width may be output. The "full width at half maximum (FWHM)" refers to the width of the wavelength at which the relative radiant intensity is 50% of the peak value in the spectral distribution of the light output. The predetermined width may have a width of, for example, less than 30 nm, and is typically 20 nm. When the normalized spectroscopic index (NDSI) described later is used, it is more preferable that the value is smaller. For example, the predetermined width is 10 nm. Alternatively, a predetermined number k corresponding to one-to-one corresponding to the wavelength λk or the wavelength band Bk may be output. By associating the number k with an optical filter that transmits the wavelength λk or the wavelength band Bk, for example, the optical filter can be easily determined from the number k. Optical filters are used in item [1.2.2].

Here, the details of step S12 will be described with reference to FIG. 14. Step S12 is a process of determining a plurality of wavelengths having a strong correlation with the future harvest amount and/or harvest time of rice when the plant is measured under the user measurement condition U.

Figure 14:
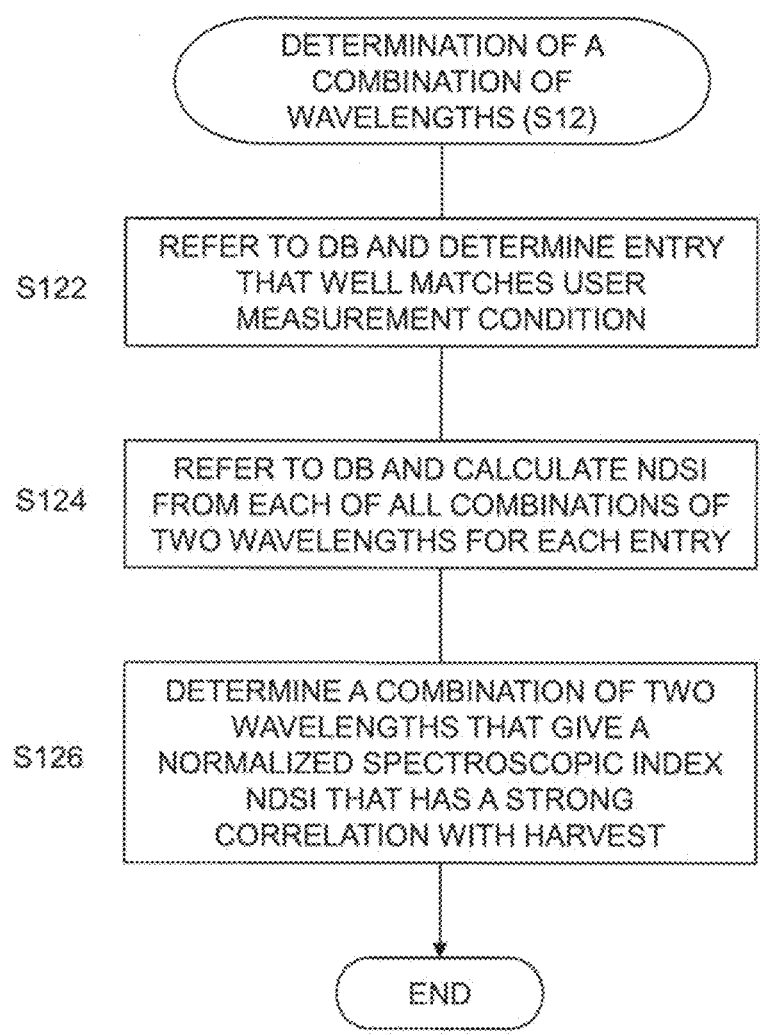
FIG. 14 is a flowchart showing details of the process in step S12 of FIG. 13.

FIG. 14 is a flowchart showing the details of the process of step S12.

In step S122, the CPU 21 refers to the database DB1 and determines an entry that well matches the user measurement condition U. For example, when the database DB1 includes entries relating to rice of a plurality of varieties, the reference range of the database DB1 is set to the entries of rice of the same variety based on the information of the rice varieties included in the user measurement condition U. Then, the CPU 21 determines an entry that matches or is close to the user measurement condition U from the reference range of the database DB1. Comparisons regarding matching are made, for example, on the date and time when the user plans to measure the rice, the azimuthal angle difference between the sun and the image pickup device (Az), the elevation angle of the image pickup device (θ1), and the elevation angle of the sun (θ2). The CPU 21 may determine that the user measurement condition U and the entry in the database DB1 are "close entries" when they are within a predetermined allowable range, for example, 5% or less. It is not necessary to compare the locations of paddy fields. This is because what is being tried is to find a combination of wavelengths that have a strong correlation with the harvest amount of the rice.

In step S124, the CPU 21 refers to the database DB1 and obtains the normalized spectroscopic index NDSI from each of all combinations of the two wavelengths for each entry. The Normalized Difference Spectral Index NDSI is an index value for a set of two wavelengths. Now, the normalized spectroscopic index NDSI for the wavelengths λ1 and λ2 among the wavelengths λ1, λ2, . . . , λ100 described in each entry shown in FIG. 2 will be described. The normalized spectroscopic index NDSI can be calculated by the following equation using the wavelengths λ1 and λ2.

$$NDSI = \frac{I(\lambda 1) - I(\lambda 2)}{I(\lambda 1) + I(\lambda 2)} \qquad \text{[Equation 1]}$$

In Equation 1, I(λ) represents reflectance with respect to wavelength λ. The reflectance I(λ) is defined by the following equation using the sunlight intensity S(λ) and the reflection intensity O(λ) of the plant shown in FIG. 2.

$$I(\lambda) = \frac{O(\lambda)}{S(\lambda)} \qquad \text{[Equation 2]}$$

According to Equation 2, the reflectances I(λ1) and I(λ2) are determined for each of the wavelengths λ1 and λ2, and as a result, the normalized spectroscopic index NDSI(λ1, λ2) for the wavelengths λ1 and λ2 is determined by Equation 1.

In the same procedure, the CPU 21 determines the normalized spectroscopic exponents NDSI(λ1, λ3), NDSI(λ1, λ4), . . . , NDSI(λ1, λ100), NDSI(λ2, λ1), . . . , NDSI (All NDSIs are obtained for λ2, λ100), . . . , NDSI(λ100, λ99). The combination NDSI(λ, λ) of the same wavelength was excluded.

Next, in step S126, the CPU 21 determines a combination of two wavelengths that give a normalized spectroscopic index NDSI that has a strong correlation with the harvest. The formula for obtaining the correlation coefficient R is as follows.

$$R = \frac{Sxy}{Sx \cdot Sy} = \frac{\frac{1}{n}\sum_{i=1}^{n}(x_i - \bar{x})(y_i - \bar{y})}{\sqrt{\frac{1}{n}\sum_{i=1}^{n}(x_i - \bar{x})^2}\sqrt{\frac{1}{n}\sum_{i=1}^{n}(y_i - \bar{y})^2}} \qquad \text{[Equation 3]}$$

The meaning of each character is as follows.
Sxy: Covariance of x and y
Sx: Standard deviation of x
Sy: Standard deviation of y
N: Total number of 2-variable data (x, y)
Xi, yi: Respective numerical values of x and y
X and the bar "-" above it, y and the bar "-" above it: the average value of x and y In the present embodiment, x is a normalized spectroscopic index and y is harvest amount. More specifically, xi is the normalized spectroscopic indices NDSI(λp, λq) obtained from the wavelengths λp and λq measured at various locations i at the date and time specified by the user measurement conditions. And yi is a value of the harvest amount for each place i. The place i may be a different field or may be a different position in the same field. Note that it is necessary that the harvest amount data is recorded for each location i. The value of the harvest amount may be the monthly or the year-round. The fineness (i.e., resolution) of the harvest amount value can be a unit of prediction when predicting the rice harvest amount for the user. Next, the CPU 21 obtains the normalized spectroscopic index NDSI based on the combination of two wavelengths different from (λp, λq), and obtains the correlation coefficient with the harvest amount. In this way, the normalized spectroscopic index NDSI is calculated for the combination of two different wavelengths. Then the correlation coefficient with the harvest amount is calculated. Accordingly, the correlation coefficient between the normalized spectroscopic index NDSI and the harvest amount is calculated for all wavelength sets. Then, the CPU 21 determines a combination of wavelengths that gives a strong correlation from the obtained correlation coefficient. When determining the two wavelengths, the wavelengths that give the strongest correlation may be determined. When determining the four wavelengths, the upper two sets of wavelengths that give the strongest correlation may be determined.

In the present embodiment, the strong correlation between the normalized spectroscopic index NDSI and the harvest amount means that the correlation coefficient is 0.7 or more. When seeking a stronger correlation, for example, it means that the correlation coefficient is 0.9 or more.

In the above example, the inventors adopted the normalized spectroscopic index NDSI as an index value. The reason is that the difference between the predicted harvest amount and the actual harvest amount is small, that is, the accuracy of the predicted result is high. For example, it is conceivable to use the vegetation index (NDVI) instead of this normalized difference index NDSI. The vegetation index NDVI can be defined as follows.

$$NDVI = \frac{NIR - R}{NIR + R} \quad \text{[Equation 4]}$$

Here, "NIR" represents an average value in a wavelength band near infrared. R means the average value in the red band.

The vegetation index NDVI is known as a value that reflects various conditions such as plant activation. It has been long believed to be useful when evaluating the growth of plants. However, when the present inventors investigated the correlation between the vegetation index NDVI and the harvest amount, the correlation coefficient R was about 0.5. It was revealed that there was only a very weak correlation or a correlation.

In addition, in the vegetation index NDVI, the wavelength range is about 50 to 100 nm, which is relatively wide, so it is considered difficult to identify a strong correlation. In the present embodiment, since the wavelength band having a predetermined width including each wavelength is 10 nm, it is possible to specify the wavelength or the wavelength band having a strong correlation with the harvest amount.

Figure 15:
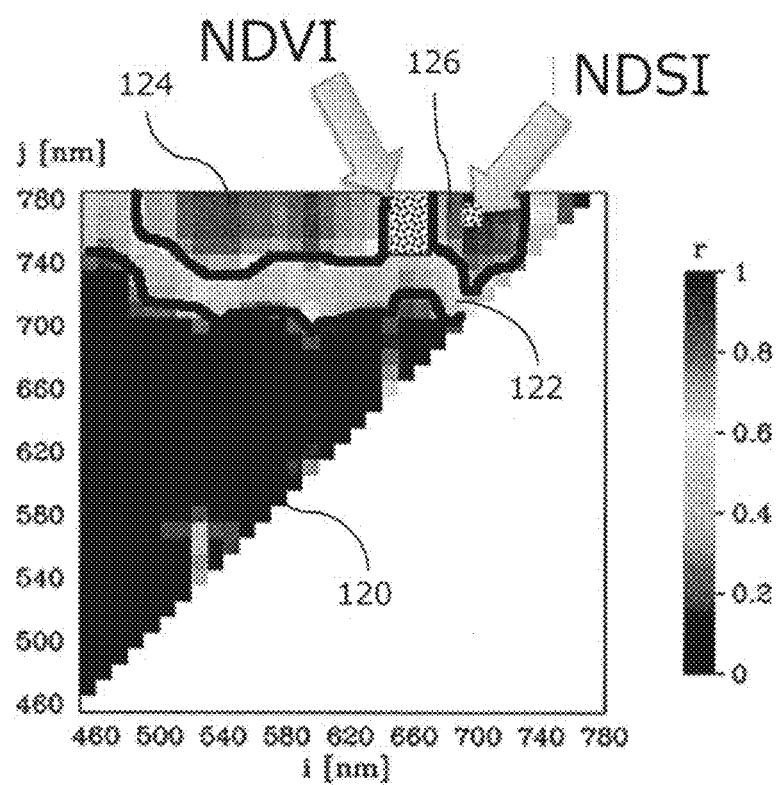
FIG. 15 is a heat map showing magnitude of a correlation coefficient between the normalized difference spectral index NDSI(i, j) and the harvest amount.

FIG. 15 shows a heat map of the correlation coefficient between the normalized spectroscopic index NDSI(i, j) and the harvest amount. The horizontal axis represents the wavelength i (nm), and the vertical axis represents the wavelength j (nm). The value of the correlation coefficient is expressed by the color depth.

In FIG. 15, for convenience of explanation, boundaries are provided in the numerical range of the correlation coefficient to form regions. Specifically, the region 120 includes a value having a correlation coefficient of less than 0.3. The region 122 includes a value having a correlation coefficient of 0.3 or more and less than 0.6. The regions 124 and 126 include regions having a correlation coefficient of 0.6 or more.

The normalized spectroscopic index NDSI obtained by the above method is i=690 (nm) and j=766 (nm), the correlation coefficient is 0.9 or more, and it belongs to the region 126.

On the other hand, the correlation between the vegetation index NDVI and the harvest amount is in the range of about 0.5 to 0.6 and belongs to the region 122. The wavelength band for obtaining the vegetation index NDVI is larger than that of the normalized difference index NDSI. The respective ranges of the normalized difference vegetation index NDSI and the vegetation index NDVI on FIG. 15 reflect the breadth of the wavelength band.

In this embodiment, two wavelengths are selected, and the future harvest amount of rice is predicted from the current image of rice taken with respect to those wavelengths. In the verification by the present inventors, it was confirmed that the prediction accuracy when two wavelengths are selected using the normalized difference index NDSI is higher than the prediction accuracy when two wavelengths are selected using the vegetation index NDVI. The details of the estimation process will be described below.

[1.2.2 Estimating Processing for Future Plants Using Information Processing System]

Figure 16:
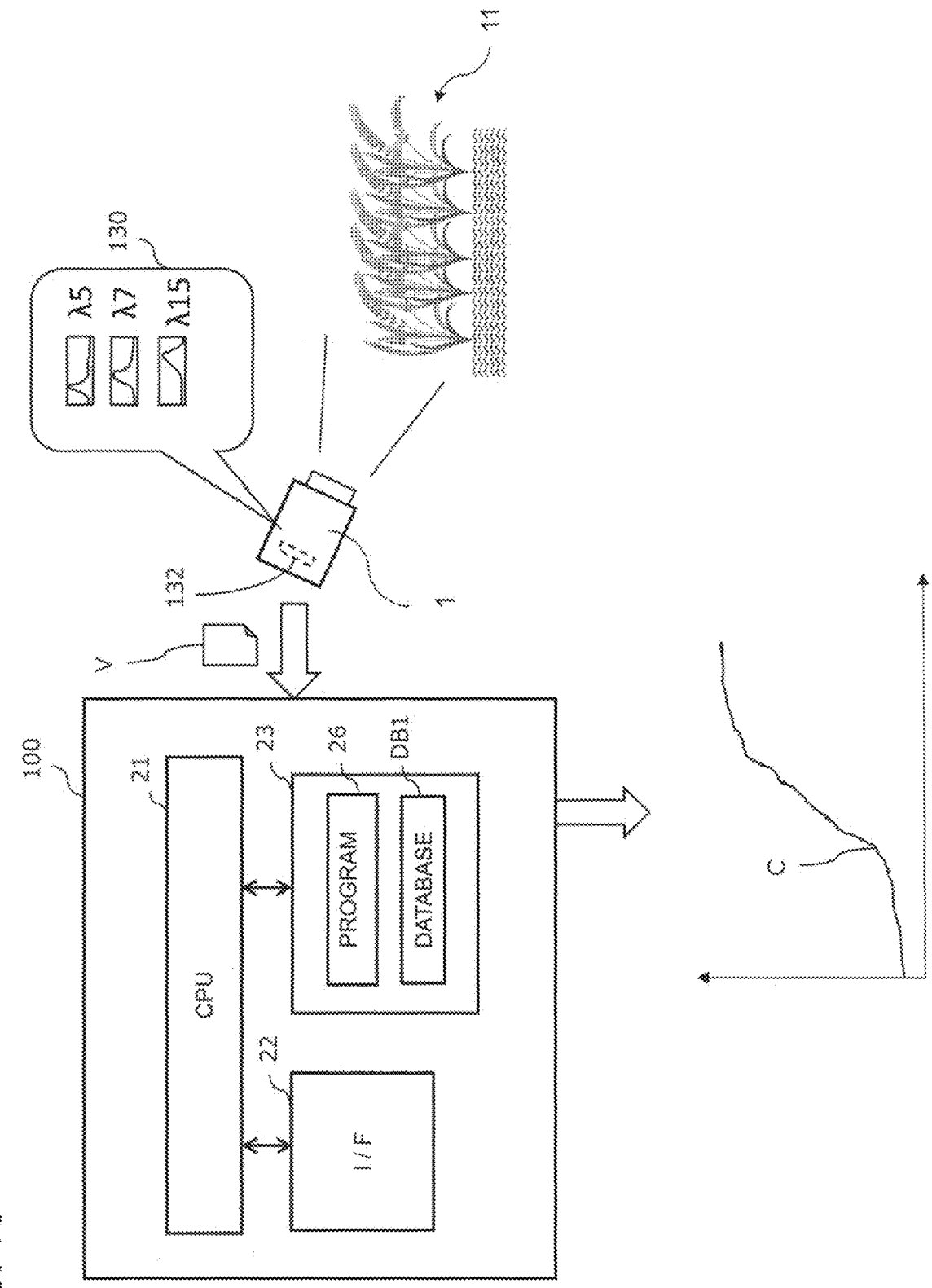
FIG. 16 is a hardware configuration diagram that can be used in a prediction process for a future of the plant using an information processing system.

FIG. 16 is a hardware configuration diagram used for estimation processing of future plants using the information processing system 100. When the rice is shot by the spectroscopic measuring instrument 1, the information processing system 100 estimates the future harvest amount of the rice based on the image information or the like acquired by the image information. Hereinafter, a more detailed description will be given.

The information processing system 100 receives the measurement conditions applied when the image information of the rice was acquired from the spectroscopic measuring instrument 1. The information processing system 100 accepts the measurement conditions and predicts the harvest amount of rice based on the measurement conditions. In FIG. 16, as the output of the information processing system 100, a harvest amount curve C in which the horizontal axis is the time and the vertical axis is the predicted harvest amount is schematically shown. The measurement conditions will be described in detail below.

First, the spectroscopic measuring instrument 1 has one or a plurality of optical filters 130 that transmit the light with a plurality of wavelengths, and one or a plurality of image sensors 132 that output signals according to the intensity of the incident light. The one or more optical filters 130 are configured to transmit the light with a plurality of wavelengths determined to have a strong correlation in the above item [1.2.1]. That is, as a result of the processing of the above-mentioned item [1.2.1], one or a plurality of optical filters 130 that transmit each wavelength are selected and set in the spectroscopic measuring instrument 1 based on the determined plurality of wavelengths. Further, the spectroscopic measuring instrument 1 can also disperse sunlight into respective predetermined wavelengths and measure the light intensity for each wavelength.

One or more image sensors 132 of the spectroscopic measuring instrument 1 detect each light transmitted through one or more optical filters 130, and output a signal according to the intensity of the light. As a result, image information based on light corresponding to the transmission wavelength of one or more optical filters 130 is generated. The image information corresponding to each transmission wavelength represents the intensity of the reflected light from the plant.

Further, the one or more image sensors 132 detect the intensity of each wavelength of the sunlight dispersed into each predetermined wavelength and generate image information. The image information corresponding to each wavelength represents the intensity of the reflected light for each wavelength from the plant. The intensity of each transmission wavelength of one or more of these optical filters 130 represents the reflection intensity of the plant obtained for each wavelength.

Further, at the time of measurement by the spectroscopic measuring instrument 1, as described with reference to FIGS. 8A to 8E and FIG. 9, in the case of rice, the spectroscopic measuring instrument 1 measures with a dip angle of 15° or less. The dip angle corresponds uniquely to the elevation angle, and the elevation angle ($\theta 1$) obtained based on the dip angle constitutes a part of the above-mentioned imaging conditions. Further, the azimuthal angle difference (Az) between the sun as the light source 12 and the spectroscopic measuring instrument 1, and the elevation angle ($\theta 2$) of the sun are also determined at the time of measurement by the spectroscopic measuring instrument 1.

From the above, the measurement conditions may include data of: the intensity of light of multiple wavelengths at the time of measurement; the intensity of reflected light from the plant; the azimuthal angle difference between the light source and the spectroscopic measuring instrument; the elevation angle of the spectroscopic measuring instrument; and the elevation angle of the light source.

Figure 17:
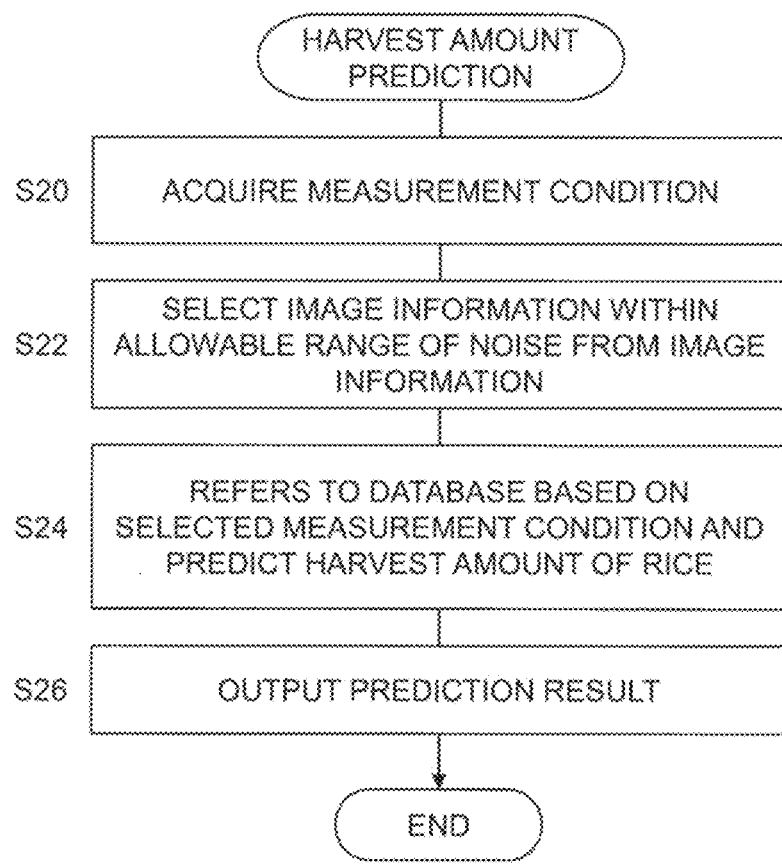
FIG. 17 is a flowchart showing a procedure of the information processing system for predicting the harvest amount of rice.

FIG. 17 is a flowchart showing a processing procedure of the information processing system 100 for predicting the future harvest amount of rice.

In step S20, the CPU 21 acquires the measurement condition V from the spectroscopic measuring instrument 1 via the I/F 22.

In step S22, the CPU 21 selects image information within an allowable range of noise from image information based on light corresponding to the transmission wavelength of one or a plurality of optical filters 130 included in the measurement condition V. For example, when the user takes a picture using the spectroscopic measuring instrument 1 with a dip angle which is larger than expected, the image information may include a subject other than rice such as the ground or the water surface. Since it contains more color components (i.e., noise components) that are closer to black than the original color of rice, that is, green, it is presumed that the intensity of the reflected light from the rice cannot be obtained accurately. In preparation for such a case, it is conceivable to set a threshold value for recognizing the noise component. According to this, when the number of pixels closer to black than the threshold value occupies a predetermined ratio or more or an absolute number, the CPU 21 does not use the image information as a basis for prediction as an image containing a large amount of noise components.

In step S24, the CPU 21 refers to the database based on the selected measurement condition V and predicts the harvest amount of rice. In this process as well, the CPU 21 refers to the database DB1 to determine an entry that matches the measurement condition V well. The method for determining this "well-matched entry" is the same as the process in step S122 of FIG. 13. The well-matched entry describes the harvest amount value. The CPU 21 extracts the value as a prediction result.

In step S26, the CPU 21 outputs the prediction result via the I/F 22. As an output method, for example, image data or character data for displaying the prediction information is transmitted to the user terminal 200 shown in FIG. 12.

By the above processing, the information processing system 100 can predict the harvest amount based on the measurement condition V including the image information for each of the predetermined plurality of wavelengths acquired by using the spectroscopic measuring instrument 1. Since there is a strong correlation between the plurality of wavelengths and the harvest amount, the prediction accuracy is sufficiently high.

Figure 18:
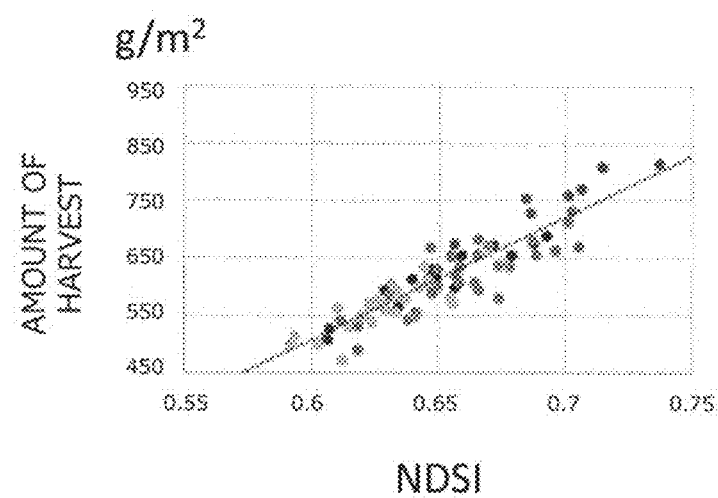
FIG. 18 is a diagram showing a relationship between the NDSI in July of a certain year and harvest amount in September for varieties of the rice plant.

The present inventors made a prediction of the harvest amount by selecting a plurality of wavelengths using the normalized spectroscopic index NDSI not only for one variety of rice but also for a plurality of other varieties, and by acquiring image information of the wavelength. Then, it was confirmed that the harvest amount could be predicted with an accuracy of 90% or more. FIG. 18 shows the relationship between the normalized spectroscopic index NDSI in July of a certain year and the harvest amount in September for a plurality of varieties. The horizontal axis shows the normalized spectroscopic index NDSI for two specific wavelengths, and the vertical axis shows the harvest amount (g/m2). The difference in varieties is expressed by the difference in color. In FIG. 18, the approximate straight line is shown by a broken line. It is understood that each point is distributed along an approximate straight line regardless of the variety. That is, it can be said that it is possible to predict the harvest amount without being greatly affected by the difference in varieties by using the normalized spectroscopic index NDSI based on two specific wavelengths.

In the above description, when determining a plurality of wavelengths having a strong correlation with the future harvest amount of rice, an entry in the database DB1 that closely matches the user measurement condition U was determined (FIG. 14). Since each entry in the database DB1 is an actually measured value, it may be difficult to cover all measurement conditions. Therefore, new entries may be generated from a plurality of existing entries by performing interpolation or extrapolation interpolation. Specifically, the CPU 21 performs interpolation or extrapolation based on the elevation angle of the sun in the measurement condition data of the database DB1, the elevation angle of the spectroscopic measuring instrument 1, and the azimuthal angle difference between the spectroscopic measuring instrument 1 and the sun, thus the resultant data after interpolation or extrapolation matches with the data about the angles included in the user measurement conditions. Then, by performing the same interpolation or extrapolation on the spectrum data, and by using the new spectrum data obtained by the interpolation, a plurality of wavelengths can be determined.

The newly generated entry may or may not be incorporated in the database DB1. The CPU 21 may only be temporarily generated and used as a virtual entry in the processing of FIG. 14 or the like.

Similarly, interpolation or extrapolation may be performed when predicting future plant conditions and/or harvests. Specifically, the CPU 21 performs interpolation or extrapolation based on the elevation angle of the sun in the measurement condition data of the database DB1, the elevation angle of the spectroscopic measuring instrument 1, and the azimuthal angle difference between the spectroscopic measuring instrument 1 and the sun. By interpolation or extrapolation, the data of the azimuthal angle difference between the sun as the light source 12 and the spectroscopic measuring instrument 1, the elevation angle of the spectroscopic measuring instrument 1, and the elevation angle of the sun, which are included in the imaging condition V, can be matched. Then, the CPU 21 may perform the same interpolation or extrapolation on the plant status data and/or the harvest data, and use the data to predict the future status and/or the harvest of the plant.

2. MODIFICATION EXAMPLE

The embodiment of the present disclosure is not limited to the above embodiment. The above-described embodiment can be variously changed according to the design and the like as long as the subject of the present disclosure can be achieved. The following is a list of modified examples of the above embodiment. The modifications described below can be applied in combination as appropriate.

So far, rice is mainly illustrated as an example. The technique according to the present disclosure can be applied to plants other than rice, and can also be used for prediction other than harvest amount prediction. An example confirmed by the present inventors is shown below.

First, soybeans is taken as an example of other plants. The present inventor considered applying the above method to soybean.

Figure 19:
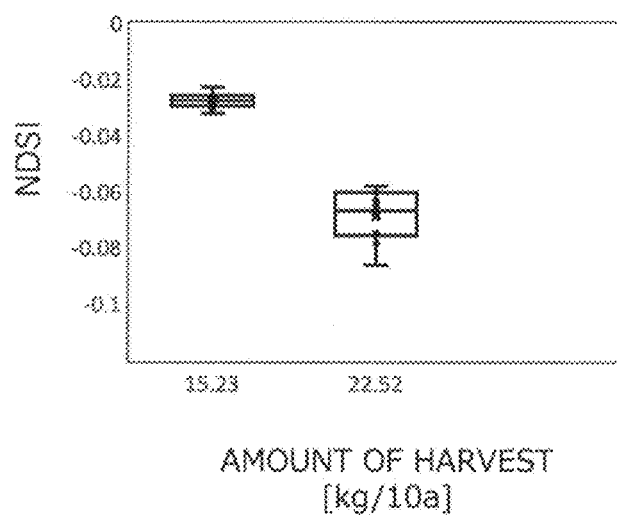
FIG. 19 is a diagram showing a relationship between the NDSI and the harvest amount of soybeans.

FIG. 19 is a diagram showing the relationship between the normalized spectroscopic index NDSI and the harvest amount of soybeans. The horizontal axis represents the harvest amount. The unit is the number of kilograms per 10 ares. As shown, different harvest amount result in different normalized spectroscopic indices (NDSIs). The present inventors have found that for soybeans, the correlation coefficient between the normalized spectroscopic index NDSI of "specific two wavelengths" and the harvest amount is as strong as 0.94. The "specific two wavelengths" can be determined by the method of the embodiment described above. By predicting the harvest amount using such a two-wavelength normalized spectroscopic index NDSI, the present inventors have confirmed that the harvest amount can be predicted with an accuracy of 90% or more.

If the harvest amount predicted using the normalized spectroscopic index NDSI of a specific two wavelengths is lower than expected, the soybean farmer can rework the cultivation plan so as to contribute more to the harvest amount. For example, by applying fertilizer, it is possible to make a prediction again after a certain period of time and determine whether or not the harvest amount is improved.

Next, an example of predicting the occurrence of pests on other plants will be described.

Figure 20A:
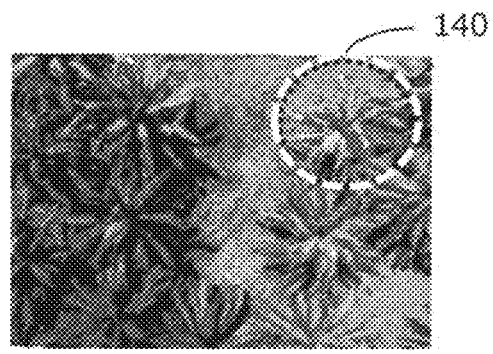
FIG. 20A is a diagram showing an image taken from the air above an oil palm cultivation area.

FIG. 20A shows an image taken from the sky above the oil palm cultivation area. It is known that some oil palms 140 have pests.

The present inventors first constructed a database DB1 for oil palm. In the database DB1, data indicating the degree of occurrence of pests is described in the item of pests in the vegetative status data for each entry. The data showing the degree of pest occurrence is divided into four stages, for example, 0 to 3. When determining the correlation coefficient, the normalized spectroscopic index NDSI and the degree of pest occurrence are used.

The present inventors determine a normalized spectroscopic index NDSI having a correlation coefficient of 0.9 or more by the same method as described above using spectral data and measurement condition data, and give the normalized spectroscopic index NDSI. Multiple wavelengths were determined. The outbreak of pests was predicted by measuring the cultivation area of oil palm with the spectroscopic measuring instrument 1 using an optical filter that transmits the wavelength.

Figure 20B:
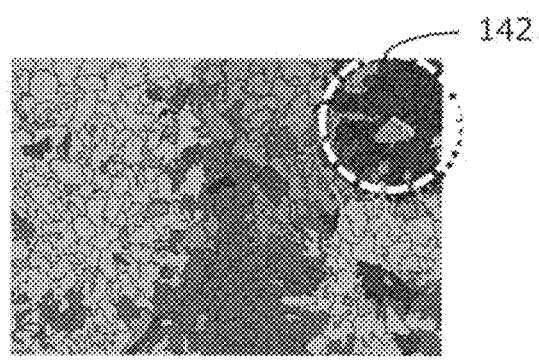
FIG. 20B is a diagram showing prediction results concerning a degree of disease and pest outbreak.

FIG. 20B shows future prediction results regarding the degree of pest outbreak. Trees that are more likely to have pests are displayed in darker colors. It is understood that the color of the vegetation area 142 of the oil palm 140 in FIG. 20A is darkly displayed. According to this method, it was possible to discriminate trees with pests with an accuracy of 87% or more.

Figure 21A:
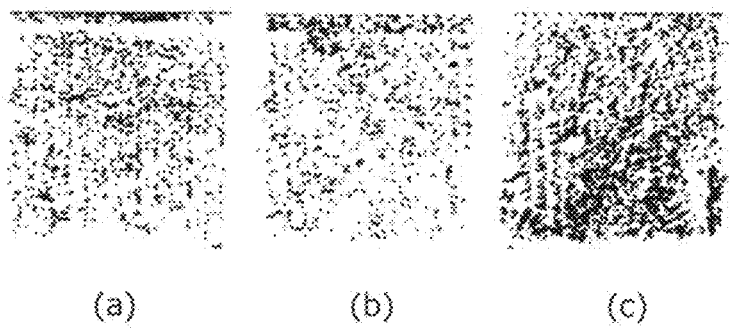
FIG. 21A is a diagram showing examples of aerial photographs showing progresses of brown blotch disease of sugar beet.

FIG. 21A is an example of an aerial photograph showing the progress of brown blotch disease of sugar beet. The photo is monochrome. The measurement dates are (a) on July 15, (b) on August 4, and (c) on August 26.

Based on the imaging conditions acquired prior to the time of imaging in (a), the present inventors obtained a plurality of wavelengths that give a normalized spectroscopic index NDSI that is highly correlated with brown blotch disease, and determined (a). An attempt was made to diagnose brown blotch disease during the period. In addition, a plurality of wavelengths were recalculated based on the imaging conditions acquired at the time of (a) imaging, and an attempt was made to diagnose brown blotch disease at the time of (b). Similarly, a plurality of wavelengths were recalculated based on the imaging conditions acquired at the time of imaging in (b), and an attempt was made to diagnose brown blotch disease at the time of (c).

Figure 21B:
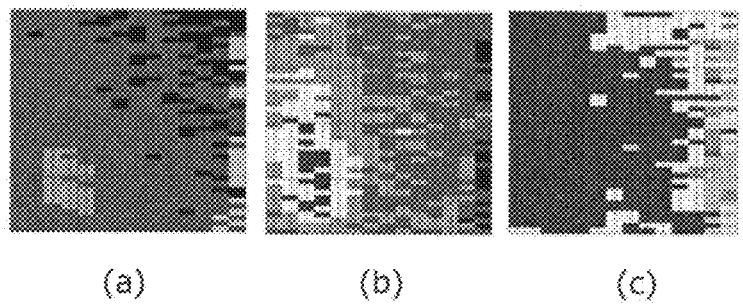
FIG. 21B is a diagram showing prediction results concerning degrees of disease and pest outbreak.

FIG. 21B shows future prediction results regarding the degree of pest outbreak. (A) to (c) of FIG. 21B show the prediction results at the same time as (a) to (c) in FIG. 21A. From the comparison between the FIG. 21A processed to black and white, and FIG. 21B, it cannot be said that it is clear that the diagnostic results correspond at first glance. However, the present inventors have confirmed that it is possible to predict brown blotch disease with higher accuracy than before. It is presumed that recalculating multiple wavelengths based on the normalized spectroscopic index NDSI every month and determining the optical filter according to the obtained wavelength contributes to more accurate prediction. As a result, it is possible to take measures for pest control on the sugar beet in the area where the pests are predicted to occur.

Figure 22:
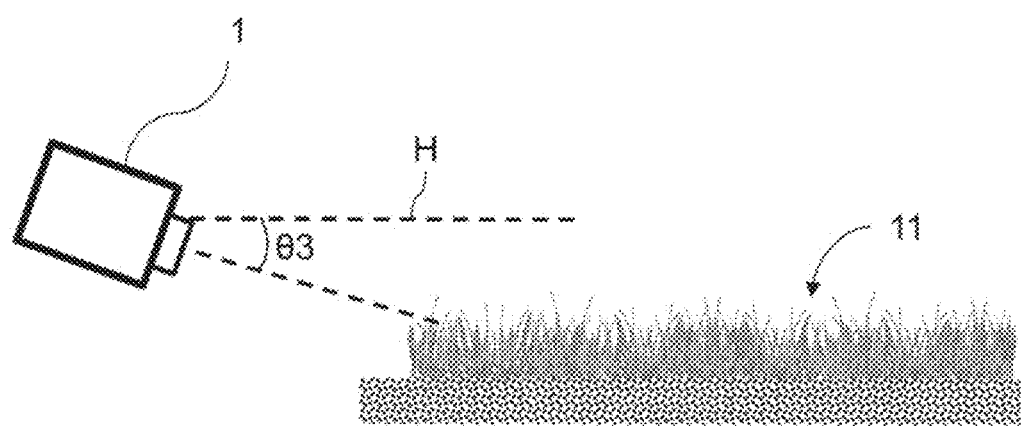
FIG. 22 is a diagram for explaining a modified example of a way of measurements.

FIG. 22 is a diagram for explaining a modified example of the measurement method. Depending on the type of plant, the dip angle when acquiring image information of grass by the spectroscopic measuring instrument 1 may change. In the case of rice, it was explained that the dip angle is preferably about 15° or less. For example, in the case of pasture, preferably, the dip angle θ3 with respect to the horizon H is an angle at which soil or water is not reflected and only the target pasture can be seen. This makes it possible to acquire image information of only grass. The present inventors have confirmed that within the range of the above-mentioned dip angle, not only the growth of grass but also the type and degree of growth of weeds mixed with grass and grass can be predicted.

3. ASPECTS

As apparent from the above embodiments and variations, the present disclosure includes the following aspects. In the following, reference signs in parenthesis are attached only for indicating a correspondence relation with the embodiment. Note that, to avoid reduction in readability, second or subsequent time of attachment of reference signs in parenthesis may be omitted.

A first aspect is an information processing system (100) including: a storage (23) that stores a database (DB1), in which spectrum data concerning light from a light source (12) and a measurement condition data at a time of measurement of the light are associated with a plant status data concerning growth of a plant (11) and/or a harvest data concerning a harvest of the plant; an interface device (22)

that receives an input of a user measurement condition which is to be applied at a time of measurement of the plant by a user and which includes data concerning angles at the time of measurement and data concerning a plant status and/or a harvest to be predicted; and a computing circuit (21) that determines at least two wavelengths contained in the light from the light source to be measured under the user measurement condition by referring to the database based on the user measurement condition.

A second aspect is the information processing system (100) based on the first aspect. In the second aspect, the computing circuit (21) determines at least two wavelength bands, each includes respective one of the at least two wavelengths of the light.

A third aspect is the information processing system (100) based on the second aspect. In the third aspect, the light source is the sun. The computing circuit (21) determines one of: bands of 30 nm or less, each of which contains respective one of the at least two wavelengths from the at least two wavelength bands contained in the light of the sun; and full width at half maximum (FWHM) of a spectrum.

A fourth aspect is the information processing system (100) based on any one of the first to third aspects. In the fourth aspect, the computing circuit (21) outputs information containing values of the at least two wavelengths.

A fifth aspect is the information processing system (100) based on any one of the first to fourth aspects. In the fifth aspect, in the database, the spectrum data includes:

a plurality of wavelengths contained in the light from the light source;
an intensity of the light per each wavelength; and
a reflection intensity of the light per each wavelength reflected by the plant, the measurement condition data, at a time when the light is measured by an measuring instrument, includes:

an elevation angle of the light source viewed from the measuring instrument;
an elevation angle of the measuring instrument; and
an azimuthal difference between the measuring instrument and the light source, in the presence of the plant status data, the plant status data includes at least one selected from:

a growth status of the plant;
a status of disease and pest occurred at the plant;
a constituent of the plant; and
a condition of soil, in which the plant grow up,
in the presence of the harvest data, the harvest data includes at least one selected from:
an amount of the harvest of the plant; and
an harvest time of the plant.

A sixth aspect is the information processing system (100) based on the fifth aspect. In the sixth aspect, the computing circuit (21) determines the at least two wavelengths by using the spectrum data associated with the measurement condition data, if the data concerning angles contained in the user measurement condition coincides with or falls within a predetermined range of:

the elevation angle of the light source;
the elevation angle of the measuring instrument; and
the azimuthal angle difference between the measuring instrument and the light source in the measurement condition data in the database.

A seventh aspect is the information processing system (100) based on the fifth aspect. In the seventh aspect, the computing circuit (21) performs an interpolation or extrapolation based on:

the elevation angle of the light source;
the elevation angle of the measuring instrument; and
the azimuthal angle difference between the measuring instrument and the light source in the measurement condition data in the database, so that the data concerning angles contained in the user measurement condition coincides with or falls within the predetermined range, and the computing circuit (21) determines the at least two wavelengths by using a spectrum data obtained by performing the same interpolation or extrapolation.

A eighth aspect is the information processing system (100) based on any one of the first to seventh aspects. In the eighth aspect, the computing circuit (21):

selects pairs of two wavelengths, the two wavelengths being different from one another and selected among the plurality of wavelengths;
calculates an index value for each of the pairs at each of a plurality of sites;
obtains a plant status and/or harvest at each of the plurality of sites;
calculates a correlation coefficient indicating a degree of correlation between the index value and the plant status and/or harvest; and
determines, as the at least two wavelengths, a pair of the two wavelengths whose correlation coefficient is equal to or more than 0.7.

A ninth aspect is the information processing system (100) based on the eighth aspect. In the ninth aspect, the computing circuit (21) determines, as the at least two wavelengths, a pair of the two wavelengths whose correlation coefficient is equal to or more than 0.9.

A tenth aspect is the information processing system (10) based on the eighth or ninth aspect. In the tenth aspect, the computing circuit (21) calculates a reflectance ratio for each of the two wavelengths from an intensity of the light and a reflection intensity of the light reflected by the plant, the each of the two wavelengths being measured under each measurement condition at the plurality of sites, and calculates a Normalized Difference Spectral Index (NDSI) for the two wavelengths using the reflectance ratio for the each wavelength.

A eleventh aspect is a spectroscopic measuring instrument (1) including: an optical filter (130) that allows the light with the at least two wavelengths determined by the information processing system (100) based on any one of the eighth to tenth aspect to pass through, and an image sensor (132) that detects the light with the at least two wavelengths.

A twelfth aspect is an information processing system (100) including: a storage (23) that stores a database (DB1), in which spectrum data concerning light from a light source and a measurement condition data at a time of measurement of the light are associated with a plant status data concerning growth of a plant and/or a harvest data concerning a harvest of the plant; an interface device (22) that receives an input of a measurement condition at a time of measurement of the plant using the spectroscopic measuring instrument (1) based on the eleventh aspect. The measurement condition includes data of: an intensity of light with the at least two wavelengths at the measurement;

an intensity of reflected light from the plant;
an azimuthal difference between the light source and the spectroscopic measuring instrument;
an elevation angle of the spectroscopic measuring instrument; and
an elevation angle of the light source, a computing circuit that predicts a plant status and/or a harvest in the future by referring to the database based on the measurement condition and each value of the at least two wavelengths.

A thirteenth aspect is the information processing system (100) based on the twelfth aspect. In the thirteenth aspect, in the database, the spectrum data includes:
  a plurality of wavelengths contained in the light from the light source;
  an intensity of the light per each wavelength; and
    a reflection intensity of the light per each wavelength reflected by the plant,
  the measurement condition data, at a time when the light is measured by the measuring instrument, includes:
    an elevation angle of the light source viewed from the measuring instrument;
    an elevation angle of the measuring instrument; and
      an azimuthal difference between the measuring instrument and the light source,
  in the presence of the plant status data, the plant status data includes at least one selected from:
    a growth status of the plant;
    a status of disease and pest occurred at the plant;
    a constituent of the plant; and
    a condition of soil, in which the plant grow up,
  in the presence of the harvest data, the harvest data includes at least one selected from:
    a harvest amount of the plant; and
    an harvest time of the plant.

A fourteenth aspect is the information processing system (100) based on the thirteenth aspect. In the fourteenth aspect, the computing circuit (21) predicts the plant status and/or harvest in the future by using the plant status and/or harvest associated with the measurement condition data, if the data concerning:
  the elevation angle of the light source;
  the elevation angle of the measuring instrument; and
  the azimuthal angle difference between the measuring instrument and the light source, contained in the measurement condition, coincides with or falls within a predetermined range of:
  the elevation angle of the light source;
  the elevation angle of the measuring instrument; and
  the azimuthal angle difference between the measuring instrument and the light source in the measurement condition data in the database.

A fifteenth aspect is the information processing system (100) based on the thirteenth aspect. In the fifteenth aspect, the computing circuit (21) performs an interpolation or extrapolation based on:
  the elevation angle of the light source;
  the elevation angle of the measuring instrument; and
  the azimuthal angle difference between the measuring instrument and the light source in the measurement condition data in the database,
  so that each of the data concerning:
    an azimuthal angle difference between the light source and the spectroscopic measuring instrument;
    an elevation angle of the spectroscopic measuring instrument; and
    an elevation angle of the light source, each contained in the measurement condition, coincides with or falls within the predetermined range, and
    the computing circuit predicts the plant status and/or harvest in the future by using the plant status data and/or harvest data by performing the same interpolation or extrapolation.

The present disclosure can be applied to an information processing system that predicts information concerning a plant status and/or harvest in the future.

What is claimed is:

1. An information processing system comprising:
  a storage that stores a database, in which spectrum data concerning light from a light source and a measurement condition data at a time of measurement of the light are associated with a plant status data concerning growth of a plant and/or a harvest data concerning a harvest of the plant;
  an interface device that receives an input of a user measurement condition which is to be applied at a time of measurement of the plant by a user and which includes data concerning angles at the time of measurement and data concerning a plant status and/or a harvest to be predicted; and
  a computing circuit that determines at least two wavelengths contained in the light from the light source to be measured under the user measurement condition by referring to the database based on the user measurement condition.

2. The information processing system of claim 1, wherein the computing circuit determines at least two wavelength bands, each includes respective one of the at least two wavelengths of the light.

3. The information processing system of claim 2, wherein the light source is the sun, and
  the computing circuit determines one of:
    bands of 30 nm or less, each of which contains respective one of the at least two wavelengths from the at least two wavelength bands contained in the light of the sun; and
    full width at half maximum(FWHM) of a spectrum.

4. The information processing system of claim 1, wherein the computing circuit outputs information containing values of the at least two wavelengths.

5. The information processing system of claim 1, wherein in the database, the spectrum data includes:
  a plurality of wavelengths contained in the light from the light source;
  an intensity of the light per each wavelength; and
  a reflection intensity of the light per each wavelength reflected by the plant,
  the measurement condition data, at a time when the light is measured by an measuring instrument, includes:
    an elevation angle of the light source viewed from the measuring instrument;
    an elevation angle of the measuring instrument; and
    an azimuthal difference between the measuring instrument and the light source,
  in the presence of the plant status data, the plant status data includes at least one selected from:
    a growth status of the plant;
    a status of disease and pest occurred at the plant;
    a constituent of the plant; and
    a condition of soil, in which the plant grow up,
  in the presence of the harvest data, the harvest data includes at least one selected from:
    an amount of the harvest of the plant; and
    an harvest time of the plant.

6. The information processing system of claim 5, wherein the computing circuit determines the at least two wavelengths by using the spectrum data associated with the measurement condition data, if the data concerning angles contained in the user measurement condition coincides with or falls within a predetermined range of:

the elevation angle of the light source;
the elevation angle of the measuring instrument; and
the azimuthal angle difference between the measuring instrument and the light source in the measurement condition data in the database.

7. The information processing system of claim 5, wherein the computing circuit performs an interpolation or extrapolation based on:
the elevation angle of the light source;
the elevation angle of the measuring instrument; and
the azimuthal angle difference between the measuring instrument and the light source in the measurement condition data in the database,
so that the data concerning angles contained in the user measurement condition coincides with or falls within the predetermined range, and
the computing circuit determines the at least two wavelengths by using a spectrum data obtained by performing the same interpolation or extrapolation.

8. The information processing system of claim 1, wherein the computing circuit:
selects pairs of two wavelengths, the two wavelengths being different from one another and selected among the plurality of wavelengths;
calculates an index value for each of the pairs at each of a plurality of sites;
obtains a plant status and/or harvest at each of the plurality of sites;
calculates a correlation coefficient indicating a degree of correlation between the index value and the plant status and/or harvest; and
determines, as the at least two wavelengths, a pair of the two wavelengths whose correlation coefficient is equal to or more than 0.7.

9. The information processing system of claim 5, wherein the computing circuit:
selects pairs of two wavelengths, the two wavelengths being different from one another and selected among the plurality of wavelengths;
calculates an index value for each of the pairs at each of a plurality of sites;
obtains a plant status and/or harvest at each of the plurality of sites;
calculates a correlation coefficient indicating a degree of correlation between the index value and the plant status and/or harvest; and
determines, as the at least two wavelengths, a pair of the two wavelengths whose correlation coefficient is equal to or more than 0.7.

10. The information processing system of claim 8, wherein the computing circuit determines, as the at least two wavelengths, a pair of the two wavelengths whose correlation coefficient is equal to or more than 0.9.

11. The information processing system of claim 9, wherein the computing circuit determines, as the at least two wavelengths, a pair of the two wavelengths whose correlation coefficient is equal to or more than 0.9.

12. The information processing system of claim 8, wherein the computing circuit
calculates a reflectance ratio for each of the two wavelengths from an intensity of the light and a reflection intensity of the light reflected by the plant, the each of the two wavelengths being measured under each measurement condition at the plurality of sites, and
calculates a Normalized Difference Spectral Index (NDSI) for the two wavelengths using the reflectance ratio for the each wavelength.

13. The information processing system of claim 9, wherein the computing circuit
calculates a reflectance ratio for each of the two wavelengths from an intensity of the light and a reflection intensity of the light reflected by the plant, the each of the two wavelengths being measured under each measurement condition at the plurality of sites, and
calculates a Normalized Difference Spectral Index (NDSI) for the two wavelengths using the reflectance ratio for the each wavelength.

14. The information processing system of claim 10, wherein the computing circuit
calculates a reflectance ratio for each of the two wavelengths from an intensity of the light and a reflection intensity of the light reflected by the plant, the each of the two wavelengths being measured under each measurement condition at the plurality of sites, and
calculates a Normalized Difference Spectral Index (NDSI) for the two wavelengths using the reflectance ratio for the each wavelength.

15. The information processing system of claim 11, wherein the computing circuit
calculates a reflectance ratio for each of the two wavelengths from an intensity of the light and a reflection intensity of the light reflected by the plant, the each of the two wavelengths being measured under each measurement condition at the plurality of sites, and
calculates a Normalized Difference Spectral Index (NDSI) for the two wavelengths using the reflectance ratio for the each wavelength.

16. A spectroscopic measuring instrument comprising:
an optical filter that allows the light with the at least two wavelengths determined by the information processing system of claim 8 to pass through, and
an image sensor that detects the light with the at least two wavelengths.

17. An information processing system comprising:
a storage that stores a database, in which spectrum data concerning light from a light source and a measurement condition data at a time of measurement of the light are associated with a plant status data concerning growth of a plant and/or a harvest data concerning a harvest of the plant;
an interface device that receives an input of a measurement condition at a time of measurement of the plant using the spectroscopic measuring instrument of claim 16, the measurement condition including data of:
an intensity of light with the at least two wavelengths at the measurement;
an intensity of reflected light from the plant;
an azimuthal difference between the light source and the spectroscopic measuring instrument;
an elevation angle of the spectroscopic measuring instrument; and
an elevation angle of the light source, a computing circuit that predicts a plant status and/or a harvest in the future by referring to the database based on the measurement condition and each value of the at least two wavelengths.

18. The information processing system of claim 17, wherein in the database, the spectrum data includes:
a plurality of wavelengths contained in the light from the light source;
an intensity of the light per each wavelength; and a reflection intensity of the light per each wavelength reflected by the plant, the measurement condition data, at a time when the light is measured by the measuring instrument, includes:

an elevation angle of the light source viewed from the measuring instrument;

an elevation angle of the measuring instrument; and an azimuthal difference between the measuring instrument and the light source, in the presence of the plant status data, the plant status data includes at least one selected from:

a growth status of the plant;

a status of disease and pest occurred at the plant;

a constituent of the plant; and a condition of soil, in which the plant grow up, in the presence of the harvest data, the harvest data includes at least one selected from:

a harvest amount of the plant; and an harvest time of the plant.

19. The information processing system of claim 18, wherein the computing circuit predicts the plant status and/or harvest in the future by using the plant status and/or harvest associated with the measurement condition data, if the data concerning:

the elevation angle of the light source;

the elevation angle of the measuring instrument; and the azimuthal angle difference between the measuring instrument and the light source, contained in the measurement condition, coincides with or falls within a predetermined range of:

the elevation angle of the light source;

the elevation angle of the measuring instrument; and the azimuthal angle difference between the measuring instrument and the light source in the measurement condition data in the database.

20. The information processing system of claim 18, wherein the computing circuit performs an interpolation or extrapolation based on:

the elevation angle of the light source;

the elevation angle of the measuring instrument; and the azimuthal angle difference between the measuring instrument and the light source in the measurement condition data in the database, so that each of the data concerning:

an azimuthal angle difference between the light source and the spectroscopic measuring instrument;

an elevation angle of the spectroscopic measuring instrument; and an elevation angle of the light source, each contained in the measurement condition, coincides with or falls within the predetermined range, and the computing circuit predicts the plant status and/or harvest in the future by using the plant status data and/or harvest data by performing the same interpolation or extrapolation.

* * * * *